(12) United States Patent
Morita et al.

(10) Patent No.: US 7,402,406 B2
(45) Date of Patent: Jul. 22, 2008

(54) METHODS OF EVALUATING PHOSPHATASE INHIBITORS

(75) Inventors: Masahiko Morita, Osaka (JP); Hiroyuki Arakawa, Osaka (JP); Mayako Yamazaki, Osaka (JP); Susumu Satoh, Osaka (JP); Shintaro Nishimura, Osaka (JP); Yasuhiro Kita, Osaka (JP); Takao Yamazaki, Osaka (JP)

(73) Assignee: Astellas Pharma Inc., Tokyo (JP)

( * ) Notice: Subject to any disclaimer, the term of this patent is extended or adjusted under 35 U.S.C. 154(b) by 383 days.

(21) Appl. No.: 10/493,057

(22) PCT Filed: Oct. 31, 2002

(86) PCT No.: PCT/JP02/11365

§ 371 (c)(1), (2), (4) Date: Jul. 19, 2004

(87) PCT Pub. No.: WO03/038118

PCT Pub. Date: May 8, 2003

(65) Prior Publication Data

US 2005/0214888 A1  Sep. 29, 2005

(30) Foreign Application Priority Data

Oct. 31, 2001  (JP) ............................. 2001-335833

(51) Int. Cl.
*C12Q 1/42* (2006.01)
*C12N 9/14* (2006.01)
*C07H 21/04* (2006.01)

(52) U.S. Cl. .................. 435/21; 435/195; 536/23.2; 536/23.5

(58) Field of Classification Search .................. 435/21, 435/195; 536/23.2, 23.5
See application file for complete search history.

(56) References Cited

FOREIGN PATENT DOCUMENTS

| EP | 1074617 | 2/2001 |
|---|---|---|
| WO | 00/55332 | 9/2000 |
| WO | 00/65068 | 11/2000 |
| WO | 01/12819 | 2/2001 |
| WO | 01/77340 | 10/2001 |
| WO | 02/20732 | 3/2002 |

OTHER PUBLICATIONS

Cohen P. T. W. Two isoforms of protein phosphatase 1 may be produced from the same gene, FEBS Letters, 1988, 232, 17-23.*
Alignment of SEQ ID No. 4 with protein Accession No. AAB94018.*
Alignment of SEQ ID No. 4 with human protein Accession No. Q9H9Z5.*
Hagiwara M. et al., Transcriptional attenuation following cAMP induction requires PP-1-mediated dephosphorylation of CREB., Cell, vol. 70, No. 1, pp. 105-113 1992.
Bito H. et al., CREB phosphorylation and dephosphorylation: a Ca (2+) -and stimulus duration-dependent switch for hippocampal gene expression. Cell, vol. 87, No. 7, pp. 1203-1214 1996.
Jane, E.B. Reusch et al., Insulin Inhibits Dephosphorylation of Adenosine 3', 5'-Monophosphate Response Element-Binding Protein/Activating Transcription Factor-1: Effect on Nuclear Phosphoserine Phosphatase-2a. Endocrinology, vol. 135, No. 6, pp. 2418-2422.
Be Wadzinski et al., Nuclear protein phosphatase 2A dephosphorylates protein kinase A-phosphorylated CREB and regulates CREB transcriptional stimulation. Molecular and Cellular Biology, vol. 13, No. 5, pp. 2822-2834 1993.
WH Wheat et al., Simian virus 40 small tumor antigen inhibits dephosphorylation of protein kinase A-phosphorylated CREB and regulates CREB transcriptional stimulation. Molecular and Cellular Biology, vol. 14, No. 9, pp. 5881-5890 1994.
Takuji Tanoue, et al., "Molecular cloning and characterization of a novel dual specificity phosphatase, MKP-5", the Journal of Biological Chemistry, vol. 274, No. 28, pp. 19949-19956 1999.

* cited by examiner

*Primary Examiner*—Rebecca E. Prouty
*Assistant Examiner*—Malgorzata A. Walicka
(74) *Attorney, Agent, or Firm*—Oblon, Spivak, McClelland, Maier & Neustadt, P.C.

(57) ABSTRACT

The present invention identified OVARC1000473 (SEQ ID NO: 1) and NT2RM1000377 (SEQ ID NO: 3) as clones showing suppression of CREB activation by forskolin, and provides evaluation methods using these genes, and/or proteins encoded by these genes. Furthermore, these proteins were found to enhance cell damage. Compounds that can be screened based on the evaluation methods of this invention are useful as agents for inhibiting the CREB dephosphorylation reaction, agents for suppressing enhancement of cell damage, and preventive and therapeutic agents for memory disorders and/or neurodegenerative disorders.

13 Claims, 4 Drawing Sheets

```
                        SEQUENCE LISTING

<160> NUMBER OF SEQ ID NOS: 6

<210> SEQ ID NO 1
<211> LENGTH: 1755
<212> TYPE: DNA
<213> ORGANISM: Homo sapiens
<220> FEATURE:
<221> NAME/KEY: CDS
<222> LOCATION: (232)..(654)

<400> SEQUENCE: 1
tgtcctgcgg gtccaggact gtccgcgggg ttgagggaag gggccgtgcc cggtgccagc      60
ccaggtgctc gcggcctggc tccatggccc tggtcacagt gagccgttcg cccccgggca     120
gcggcgcctc cacgcccgtg gggccctggg accaggcggt ccagcgaagg agtcgactcc     180
agcgaaggca gagctttgcg gtgctccgtg gggctgtcct gggactgcag g atg gag     237
                                                         Met Glu
                                                          1 ggg aca atg atg atg cag cag agg cca gtt ctg agc caa cag cac cct     285
Gly Thr Met Met Met Gln Gln Arg Pro Val Leu Ser Gln Gln His Pro
        5                   10                  15 agt ttc att ctc aac tct agc cct gca cac tca cct atg gcc cgg gag     333
Ser Phe Ile Leu Asn Ser Ser Pro Ala His Ser Pro Met Ala Arg Glu
     20                  25                  30 att gac aac ttc tac cct gag cgc ttc acc tac cac aat gtg cgc ctc     381
Ile Asp Asn Phe Tyr Pro Glu Arg Phe Thr Tyr His Asn Val Arg Leu
 35                  40                  45                  50 tgg gat gag gag tcg gcc cag ctg ctg ccg cac tgg aag gag acg cac     429
Trp Asp Glu Glu Ser Ala Gln Leu Leu Pro His Trp Lys Glu Thr His
                 55                  60                  65 cgc ttc att gag gct gca aga gca cag ggc acc cac gtg ctg gtc cac     477
Arg Phe Ile Glu Ala Ala Arg Ala Gln Gly Thr His Val Leu Val His
             70                  75                  80 tgc aag atg ggc gtc agc cgc tca gcg gcc aca gtg ctg gcc tat gcc     525
Cys Lys Met Gly Val Ser Arg Ser Ala Ala Thr Val Leu Ala Tyr Ala
         85                  90                  95 atg aag cag tac gaa tgc agc ctg gag cag gcc ctg cgc cac gtg cag     573
Met Lys Gln Tyr Glu Cys Ser Leu Glu Gln Ala Leu Arg His Val Gln
    100                 105                 110 gag ctc cgg ccc atc gcc cgc ccc aac cct ggc ttc ctg cgc cag ctg     621
Glu Leu Arg Pro Ile Ala Arg Pro Asn Pro Gly Phe Leu Arg Gln Leu
115                 120                 125                 130 cag atc tac cag ggc atc ctg acg gcc aga acc tgagggtggt ggggaggaga     674
Gln Ile Tyr Gln Gly Ile Leu Thr Ala Arg Thr
                135                 140 aggttgtagg catggaagag agccaggcag ccccgaaaga agagcctggg ccacggccac     734
gtataaacct ccgaggggtc atgaggtcca tcagtcttct ggagccctcc ttggagctgg     794
```

```
agagcacctc agagaccagt gacatgccag aggtcttctc ttcccacgag tcttcacatg      854
aagagcctct gcagcccttc ccacagcttg caaggaccaa gggaggccag caggtggaca      914 ggggcctca gcctgccctg aagtcccgcc agtcagtggt taccctccag ggcagtgccg       974
tggtggccaa ccggacccag gccttccagg agcaggagca ggggcagggg caggggcagg     1034
gagagccctg catttcctct acgcccaggt tccggaaggt ggtgagacag gccagcgtgc     1094
atgacagtgg agaggagggc gaggcctgag ccctcacaca tgcccacgct ccctgacac      1154 tgaagaggat ccacaactcc ttggagaaac accctcacgt ctgttgccgc acacattcct     1214
ctcagctccg ccccatacc gtcactacag cctcacctcc caccctgtc actacggcct       1274 cacctcccac ccctgtcact acagcctcac ctcctacagc cttaagtccc aggcccatgt     1334
ctgcctgtcc aagggctcaa gactttctaa ctgggatgtg gtagagggac tgaaggtacc     1394
tttgggggca acagcaccct agtttcattc tcaactctag ccctgcacct cctgtcctct     1454
cccagttcat tcctggaacc agccaggcca ggcaaccagt ggcccccaaa ggcaggcagg     1514
atcctcaggc cccagccgcg ggaggctgga agggctggca gatcgcttcc ctcatccacc     1574
tccaccggtc caggtctttg ctgctgtccc cagacctcct gtgacaccac gccagatcac     1634
agggcaccag gccagagata gtcttctttt tgtcctttct ggcctctggc tagtcagttt     1694
ttcatagcct tacagtatct ggctttgtac tgagaaataa aacacatttt catatttggt     1754
t                                                                    1755

<210> SEQ ID NO 2
<211> LENGTH: 141
<212> TYPE: PRT
<213> ORGANISM: Homo sapiens

<400> SEQUENCE: 2

Met Glu Gly Thr Met Met Met Gln Gln Arg Pro Val Leu Ser Gln Gln
1               5                   10                  15

His Pro Ser Phe Ile Leu Asn Ser Ser Pro Ala His Ser Pro Met Ala
            20                  25                  30

Arg Glu Ile Asp Asn Phe Tyr Pro Glu Arg Phe Thr Tyr His Asn Val
        35                  40                  45

Arg Leu Trp Asp Glu Glu Ser Ala Gln Leu Leu Pro His Trp Lys Glu
    50                  55                  60

Thr His Arg Phe Ile Glu Ala Ala Arg Ala Gln Gly Thr His Val Leu
65                  70                  75                  80

Val His Cys Lys Met Gly Val Ser Arg Ser Ala Ala Thr Val Leu Ala
                85                  90                  95

Tyr Ala Met Lys Gln Tyr Glu Cys Ser Leu Glu Gln Ala Leu Arg His
            100                 105                 110

Val Gln Glu Leu Arg Pro Ile Ala Arg Pro Asn Pro Gly Phe Leu Arg
        115                 120                 125

Gln Leu Gln Ile Tyr Gln Gly Ile Leu Thr Ala Arg Thr
    130                 135                 140

<210> SEQ ID NO 3
<211> LENGTH: 1007
<212> TYPE: DNA
<213> ORGANISM: Homo sapiens
<220> FEATURE:
<221> NAME/KEY: CDS
<222> LOCATION: (325)..(744)

<400> SEQUENCE: 3
```

```
aactatgttg ctgctggaga tcaatgaagc cgagtggatg ggggctgaat gtgcgagtcc    60
atagctgaag aggagcgcca gatggtggag gaatacactt atttatgaag tggacttagt   120
agttttaagc agaaccatga aaacctctgt gacaactccc tccagctcca agagtgccgg   180
gaggtggggg gcggcgcatc cgcggcctcg agcttgctac ctcagcccat ccccaccacc   240
cctgacatcg agaacgctga gctcaccccc atcttgccct tcctgttcct tggcaatgag   300
caggatgctc aggacctgga cacc atg cag cgg ctg aac atc ggc tac gtc      351
                           Met Gln Arg Leu Asn Ile Gly Tyr Val
                             1               5 atc aac gtc acc act cat ctt ccc ctc tac cac tat gag aaa ggc ctg     399
Ile Asn Val Thr Thr His Leu Pro Leu Tyr His Tyr Glu Lys Gly Leu
 10              15                  20                  25 ttc aac tac aag cgg ctg cca gcc act gac agc aac aag cag aac ctg     447
Phe Asn Tyr Lys Arg Leu Pro Ala Thr Asp Ser Asn Lys Gln Asn Leu
                 30                  35                  40 cgg cag tac ttt gaa gag gct ttt gag ttc att gag gaa gct cac cag     495
Arg Gln Tyr Phe Glu Glu Ala Phe Glu Phe Ile Glu Glu Ala His Gln
             45                  50                  55 tgt ggg aag ggg ctt ctc atc cac tgc cag gct ggg gtg tcc cgc tcc     543
Cys Gly Lys Gly Leu Leu Ile His Cys Gln Ala Gly Val Ser Arg Ser
         60                  65                  70 gcc acc atc gtc atc gct tac ttg atg aag cac act cgg atg acc atg     591
Ala Thr Ile Val Ile Ala Tyr Leu Met Lys His Thr Arg Met Thr Met
     75                  80                  85 act gat gct tat aaa ttt gtc aaa ggc aaa cga cca att atc tcc cca     639
Thr Asp Ala Tyr Lys Phe Val Lys Gly Lys Arg Pro Ile Ile Ser Pro
 90                  95                 100                 105 aac ctt aac ttc atg ggg cag ttg cta gag ttc gag gaa gac cta aac     687
Asn Leu Asn Phe Met Gly Gln Leu Leu Glu Phe Glu Glu Asp Leu Asn
                110                 115                 120 aac ggt gtg aca ccg aga atc ctt aca cca aag ctg atg ggc gtg gag     735
Asn Gly Val Thr Pro Arg Ile Leu Thr Pro Lys Leu Met Gly Val Glu
            125                 130                 135 acg gtt gtg tgacaatggt ctggatggaa aggattgctg ctctccatta            784
Thr Val Val
        140 ggagacaatg aggaaggagg atggattctg gttttttttc tttctttttt tttgtagctg   844 ggagtaagtt tgtgaatgga acaaacttg tttaaacact ttacttttaa caagtgtaag    904 aagactataa cttttgatgc cattgagatt cacctcccac aaactgacaa attaaggagg   964 ttaaagaagt aattttttta agccaacaat aaaaatataa tac                    1007
```

<210> SEQ ID NO 4
<211> LENGTH: 140
<212> TYPE: PRT
<213> ORGANISM: Homo sapiens

<400> SEQUENCE: 4

```
Met Gln Arg Leu Asn Ile Gly Tyr Val Ile Asn Val Thr Thr His Leu
 1               5                  10                  15

Pro Leu Tyr His Tyr Glu Lys Gly Leu Phe Asn Tyr Lys Arg Leu Pro
             20                  25                  30

Ala Thr Asp Ser Asn Lys Gln Asn Leu Arg Gln Tyr Phe Glu Glu Ala
         35                  40                  45

Phe Glu Phe Ile Glu Glu Ala His Gln Cys Gly Lys Gly Leu Leu Ile
     50                  55                  60
```

```
His Cys Gln Ala Gly Val Ser Arg Ser Ala Thr Ile Val Ile Ala Tyr
 65                  70                  75                  80

Leu Met Lys His Thr Arg Met Thr Met Thr Asp Ala Tyr Lys Phe Val
                 85                  90                  95

Lys Gly Lys Arg Pro Ile Ile Ser Pro Asn Leu Asn Phe Met Gly Gln
            100                 105                 110

Leu Leu Glu Phe Glu Glu Asp Leu Asn Asn Gly Val Thr Pro Arg Ile
        115                 120                 125

Leu Thr Pro Lys Leu Met Gly Val Glu Thr Val Val
    130                 135                 140

<210> SEQ ID NO 5
<211> LENGTH: 2051
<212> TYPE: DNA
<213> ORGANISM: Homo sapiens
<220> FEATURE:
<221> NAME/KEY: CDS
<222> LOCATION: (285)..(1733)
<220> FEATURE:
<221> NAME/KEY: misc_feature
<222> LOCATION: (1955)..(1955)
<223> OTHER INFORMATION: n is a, c, g, or t
<220> FEATURE:
<221> NAME/KEY: misc_feature
<222> LOCATION: (2011)..(2011)
<223> OTHER INFORMATION: n is a, c, g, or t
<220> FEATURE:
<221> NAME/KEY: misc_feature
<222> LOCATION: (2033)..(2033)
<223> OTHER INFORMATION: n is a, c, g, or t

<400> SEQUENCE: 5
tcactatagg gcgaattggg cctctagatg catgctcgag cggccgccag tgtgatggat      60
atctgcagaa ttcgcccttt cgatttaggt gacactatag aaggtacgcc tgcaggtacc     120
ggtccggaat tcccgggtcg acccacgcgt ccgcaatgaa gccgagtgaa tgggggctga     180
atgtgcgagt ccatagctga agaggagcgc agatggtgg aggaatacac ttatttatga      240
aactgtcttg agttcttctt gaattgccag ttttcagcct ctc atg cct ccg tct        296
                                              Met Pro Pro Ser
                                                1 cct tta gac gac agg gta gta gtg gca cta tct agg ccc gtc cga cct        344
Pro Leu Asp Asp Arg Val Val Val Ala Leu Ser Arg Pro Val Arg Pro
  5                  10                  15                  20 cag gat ctc aac ctt tgt tta gac tct agt tac ctt ggc tct gcc aac        392
Gln Asp Leu Asn Leu Cys Leu Asp Ser Ser Tyr Leu Gly Ser Ala Asn
                 25                  30                  35 cca ggc agt aac agc cac cct cct gtc atc gcc acc acc gtt gtg tcc        440
Pro Gly Ser Asn Ser His Pro Pro Val Ile Ala Thr Thr Val Val Ser
             40                  45                  50 ctc aag gct gcg aat ctg acg tat atg ccc tca tcc agc ggc tct gcc        488
Leu Lys Ala Ala Asn Leu Thr Tyr Met Pro Ser Ser Ser Gly Ser Ala
         55                  60                  65 cgc tcg ctg aat tgt gga tgc agc agt gcc agc tgc tgc act gtg gca        536
Arg Ser Leu Asn Cys Gly Cys Ser Ser Ala Ser Cys Cys Thr Val Ala
     70                  75                  80 acc tac gac aag gac aat cag gcc caa acc caa gcc att gcc gct ggc        584
Thr Tyr Asp Lys Asp Asn Gln Ala Gln Thr Gln Ala Ile Ala Ala Gly
 85                  90                  95                 100 acc acc acc act gcc atc gga acc tct acc acc tgc cct gct aac cag        632
Thr Thr Thr Thr Ala Ile Gly Thr Ser Thr Thr Cys Pro Ala Asn Gln
                105                 110                 115 atg gtc aac aat aat gag aat aca ggc tct cta agt cca tca agt ggg        680
```

```
                                                                              -continued Met Val Asn Asn Asn Glu Asn Thr Gly Ser Leu Ser Pro Ser Ser Gly
            120                 125                 130 gtg ggc agc cct gtg tca ggg acc ccc aag cag cta gcc agc atc aaa          728
Val Gly Ser Pro Val Ser Gly Thr Pro Lys Gln Leu Ala Ser Ile Lys
        135                 140                 145 ata atc tac ccc aat gac ttg gca aag aag atg acc aaa tgc agc aag          776
Ile Ile Tyr Pro Asn Asp Leu Ala Lys Lys Met Thr Lys Cys Ser Lys
150                 155                 160 agt cac ctg ccg agt cag ggc cct gtc atc att gac tgc agg ccc ttc          824
Ser His Leu Pro Ser Gln Gly Pro Val Ile Ile Asp Cys Arg Pro Phe
165                 170                 175                 180 atg gag tac aac aag agt cac atc caa gga gct gtc cac att aac tgt          872
Met Glu Tyr Asn Lys Ser His Ile Gln Gly Ala Val His Ile Asn Cys
            185                 190                 195 gcc gat aag atc agc cgg cgg aga ctg cag cag ggc aag atc act gtc          920
Ala Asp Lys Ile Ser Arg Arg Arg Leu Gln Gln Gly Lys Ile Thr Val
        200                 205                 210 cta gac ttg att tcc tgt agg gaa ggc aag gac tct ttc aag agg atc          968
Leu Asp Leu Ile Ser Cys Arg Glu Gly Lys Asp Ser Phe Lys Arg Ile
        215                 220                 225 ttt tcc aaa gaa att ata gtt tat gat gag aat acc aat gaa cca agc         1016
Phe Ser Lys Glu Ile Ile Val Tyr Asp Glu Asn Thr Asn Glu Pro Ser
230                 235                 240 cga gtg atg ccc tcc cag cca ctt cac ata gtc ctc gag tcc ctg aag         1064
Arg Val Met Pro Ser Gln Pro Leu His Ile Val Leu Glu Ser Leu Lys
245                 250                 255                 260 aga gaa ggc aaa gaa cct ctg gtg ttg aaa ggt gga ctt agt agt ttt         1112
Arg Glu Gly Lys Glu Pro Leu Val Leu Lys Gly Gly Leu Ser Ser Phe
            265                 270                 275 aag cag aac cat gaa aac ctc tgt gac aac tcc ctc cag ctc caa gag         1160
Lys Gln Asn His Glu Asn Leu Cys Asp Asn Ser Leu Gln Leu Gln Glu
        280                 285                 290 tgc cgg gag gtg ggg ggc ggc gca tcc gcg gcc tcg agc ttg cta cct         1208
Cys Arg Glu Val Gly Gly Gly Ala Ser Ala Ala Ser Ser Leu Leu Pro
        295                 300                 305 cag ccc atc ccc acc acc cct gac atc gag aac gct gag ctc acc ccc         1256
Gln Pro Ile Pro Thr Thr Pro Asp Ile Glu Asn Ala Glu Leu Thr Pro
310                 315                 320 atc ttg ccc ttc ctg ttc ctt ggc aat gag cag gat gct cag gac ctg         1304
Ile Leu Pro Phe Leu Phe Leu Gly Asn Glu Gln Asp Ala Gln Asp Leu
325                 330                 335                 340 gac acc atg cag cgg ctg aac atc ggc tac gtc atc aac gtc acc act         1352
Asp Thr Met Gln Arg Leu Asn Ile Gly Tyr Val Ile Asn Val Thr Thr
            345                 350                 355 cat ctt ccc ctc tac cac tat gag aaa ggc ctg ttc aac tac aag cgg         1400
His Leu Pro Leu Tyr His Tyr Glu Lys Gly Leu Phe Asn Tyr Lys Arg
        360                 365                 370 ctg cca gcc act gac agc aac aag cag aac ctg cgg cag tac ttt gaa         1448
Leu Pro Ala Thr Asp Ser Asn Lys Gln Asn Leu Arg Gln Tyr Phe Glu
        375                 380                 385 gag gct ttt gag ttc att gag gaa gct cac cag tgt ggg aag ggg ctt         1496
Glu Ala Phe Glu Phe Ile Glu Glu Ala His Gln Cys Gly Lys Gly Leu
            390                 395                 400 ctc atc cac tgc cag gct ggg gtg tcc cgc tcc gcc acc atc gtc atc         1544
Leu Ile His Cys Gln Ala Gly Val Ser Arg Ser Ala Thr Ile Val Ile
405                 410                 415                 420 gct tac ttg atg aag cac act cgg atg acc atg act gat gct tat aaa         1592
Ala Tyr Leu Met Lys His Thr Arg Met Thr Met Thr Asp Ala Tyr Lys
                425                 430                 435
```

-continued

```
ttt gtc aaa ggc aaa cga cca att atc tcc cca aac ctt aac ttc atg    1640
Phe Val Lys Gly Lys Arg Pro Ile Ile Ser Pro Asn Leu Asn Phe Met
            440                 445                 450 ggg cag ttg cta gag ttc gag gaa gac cta aac aac ggt gtg aca ccg    1688
Gly Gln Leu Leu Glu Phe Glu Glu Asp Leu Asn Asn Gly Val Thr Pro
        455                 460                 465 aga atc ctt aca cca aag ctg atg ggc gtg gag acg gtt gtg tga        1733
Arg Ile Leu Thr Pro Lys Leu Met Gly Val Glu Thr Val Val
    470                 475                 480 caatggtctg gatggaaagg attgctgctc tccattagga gacaatgagg aaggaggatg  1793
gattctggtt ttttttcttt cttttttttt tgtagttggg agtaaagttt gtgaatggaa  1853
acaaacttgg ttaaacactt tattttaac aagtgtaaga agactatact tttgatgcca   1913
ttgagattca ccttccacaa actggccaaa taaggaggt tnaagaagta attttttta    1973
agcccaacca ttaaaaattt aatacaactt ggtttctncc ccttttcct ttaaagctan   2033
tttgtaaaag tttatgag                                                2051
```

<210> SEQ ID NO 6
<211> LENGTH: 482
<212> TYPE: PRT
<213> ORGANISM: Homo sapiens

<400> SEQUENCE: 6

```
Met Pro Pro Ser Pro Leu Asp Asp Arg Val Val Ala Leu Ser Arg
1               5                   10                  15

Pro Val Arg Pro Gln Asp Leu Asn Leu Cys Leu Asp Ser Ser Tyr Leu
            20                  25                  30

Gly Ser Ala Asn Pro Gly Ser Asn Ser His Pro Pro Val Ile Ala Thr
        35                  40                  45

Thr Val Ser Leu Lys Ala Ala Asn Leu Thr Tyr Met Pro Ser Ser
    50                  55                  60

Ser Gly Ser Ala Arg Ser Leu Asn Cys Gly Cys Ser Ser Ala Ser Cys
65                  70                  75                  80

Cys Thr Val Ala Thr Tyr Asp Lys Asp Asn Gln Ala Gln Thr Gln Ala
                85                  90                  95

Ile Ala Ala Gly Thr Thr Thr Ala Ile Gly Thr Ser Thr Thr Cys
            100                 105                 110

Pro Ala Asn Gln Met Val Asn Asn Asn Glu Asn Thr Gly Ser Leu Ser
        115                 120                 125

Pro Ser Ser Gly Val Gly Ser Pro Val Ser Gly Thr Pro Lys Gln Leu
    130                 135                 140

Ala Ser Ile Lys Ile Ile Tyr Pro Asn Asp Leu Ala Lys Lys Met Thr
145                 150                 155                 160

Lys Cys Ser Lys Ser His Leu Pro Ser Gln Gly Pro Val Ile Ile Asp
                165                 170                 175

Cys Arg Pro Phe Met Glu Tyr Asn Lys Ser His Ile Gln Gly Ala Val
            180                 185                 190

His Ile Asn Cys Ala Asp Lys Ile Ser Arg Arg Leu Gln Gln Gly
        195                 200                 205

Lys Ile Thr Val Leu Asp Leu Ile Ser Cys Arg Glu Gly Lys Asp Ser
    210                 215                 220

Phe Lys Arg Ile Phe Ser Lys Glu Ile Ile Val Tyr Asp Glu Asn Thr
225                 230                 235                 240

Asn Glu Pro Ser Arg Val Met Pro Ser Gln Pro Leu His Ile Val Leu
                245                 250                 255
```

-continued

```
Glu Ser Leu Lys Arg Glu Gly Lys Glu Pro Leu Val Leu Lys Gly Gly
            260                 265                 270

Leu Ser Ser Phe Lys Gln Asn His Glu Asn Leu Cys Asp Asn Ser Leu
        275                 280                 285

Gln Leu Gln Glu Cys Arg Glu Val Gly Gly Ala Ser Ala Ala Ser
    290                 295                 300

Ser Leu Leu Pro Gln Pro Ile Pro Thr Thr Pro Asp Ile Glu Asn Ala
305                 310                 315                 320

Glu Leu Thr Pro Ile Leu Pro Phe Leu Phe Leu Gly Asn Glu Gln Asp
                325                 330                 335

Ala Gln Asp Leu Asp Thr Met Gln Arg Leu Asn Ile Gly Tyr Val Ile
            340                 345                 350

Asn Val Thr Thr His Leu Pro Leu Tyr His Tyr Glu Lys Gly Leu Phe
            355                 360                 365

Asn Tyr Lys Arg Leu Pro Ala Thr Asp Ser Asn Lys Gln Asn Leu Arg
    370                 375                 380

Gln Tyr Phe Glu Glu Ala Phe Glu Phe Ile Glu Glu Ala His Gln Cys
385                 390                 395                 400

Gly Lys Gly Leu Leu Ile His Cys Gln Ala Gly Val Ser Arg Ser Ala
                405                 410                 415

Thr Ile Val Ile Ala Tyr Leu Met Lys His Thr Arg Met Thr Met Thr
                420                 425                 430

Asp Ala Tyr Lys Phe Val Lys Gly Lys Arg Pro Ile Ile Ser Pro Asn
            435                 440                 445

Leu Asn Phe Met Gly Gln Leu Leu Glu Phe Glu Glu Asp Leu Asn Asn
    450                 455                 460

Gly Val Thr Pro Arg Ile Leu Thr Pro Lys Leu Met Gly Val Glu Thr
465                 470                 475                 480

Val Val
```

METHODS OF EVALUATING PHOSPHATASE INHIBITORS

CROSS-REFERENCE TO A RELATED APPLICATION

The present application is a National Stage (371) of International Application PCT/JP02/11365, filed on Oct. 31, 2002, which claims priority to Japanese Patent Application No. JP 2001-335833, filed on Oct. 31, 2001.

TECHNICAL FIELD

The present invention relates to methods of evaluating phosphatase inhibitors, using phosphatases that inhibit the transcriptional activity of a transcription factor (cAMP responsive element binding protein: CREB) that binds to the cyclic AMP (cAMP) responsive element (CRE). The phosphatase inhibitors obtainable using these methods increase CREB's transcriptional activity, are considered to improve memory disorders and neurodegeneration, and are expected to become pharmaceutical agents for a wide variety of neural disorders.

BACKGROUND ART

CREB is a transcription factor that binds to CRE. The Ser 133 of CREB is phosphorylated and then activated by cyclic AMP-dependent protein kinase. CRE is located in the transcription regulatory sites of gene clusters whose expression is enhanced by cAMP (somatostatin, c-fos, etc.), and is an indispensable component for the cAMP-induced induction.

CREB whose serine has been phosphorylated binds to transcription regulatory factors, mainly CREB binding proteins (CBPs), and has increased binding activity (Shaywitz, A. J. et al., Annu. Rev. Biochem. 68:821 (1999)). Furthermore, an increase of CREB's transcriptional activity has been observed on depolarization due to high $K^+$ concentration (Beitmer-Johnson, D. et al., J. Biol. Chem. 273:19834-19839 (1998)), or synapse stimulation caused by long-term enhancement (LTP) (Deisseroth, K. et al., Neuron 16:89-101 (1996)). Moreover, glutamic acid-induced neuronal calcium signals are known to increase the CREB's transcriptional activity evoked by synaptic activity (Hardingham, G. E. et al., Nat. Neurosci. 4:261-267 (2001)). In addition, results of behavioral memory experiments on Sea Hares (Aplysia) and rats revealed that CREB phosphorylation is important for memory formation (Silva, A. J. et al., Annu. Rev. Neurosci. 21:127 (1998)). Furthermore, in Alzheimer's dementia, the amount of phosphorylated CREB in the brain is significantly decreased (Yamamoto-Sasaki, M. et al., Brain Res. 824:300-303 (1999)). These findings suggest that increased CREB activity is related to memory formation.

Recently, increased CREB activity was shown to be linked to the anti-apoptosis activity of neurons. In pathological models of cerebral infarction and such, CREB phosphorylated regions were observed in the penumbra region near the infarct (Tanaka, K. et al., Brain Res. 818: 520-526 (1999)). The term "penumbra region" refers to a region around the cerebral infarcted lesion, which has decreased blood flow but continuous neural activity. In general, when conditions of insufficient blood flow to the penumbra region continue for 48 hours or more, neuron death can be observed. This fact has also been observed in experimental systems on a cellular level. An increase in CREB's transcriptional activity due to hypoxia (Beitmer-Johnson, D. et al., supra) and low glucose stimulation (Ricco, A. et al., Science 286:2358-2361 (1999)) in cultured neurons has also been confirmed. Furthermore, a survival effect due to increased CREB transcription has been confirmed in the case of neuron death caused by the removal of nutritional factors (Ricco, A. et al., supra).

CBP functions as a co-activator of CREB. CBP is known to bind to both phosphorylated CREB and to general transcription factor TFII B, to promote CREB's transcriptional activity (Shaywitz, A. J. et al., supra). Huntingtin, the product of the IT15 gene which causes Huntington's disease, and atrophin-1, the product of the gene which causes dentatorubropallidoluysian atrophy, actively bind to CBP and suppress its function (Nucifora Jr., F. C. et al., Science 291: 2423-2428 (2001)). Specifically, huntingtin and atrophin-1 have been known to suppress CREB's transcriptional activity via CBP, and to damage neurons by preventing the transcription of target genes known to be decisive in neuron survival.

In general, various cellular phenomena are known to be regulated through phosphorylation (or dephosphorylation) by protein kinases and phosphatases. Already revealed examples of such phenomena are, mechanisms regulated by phosphorylation, such as contraction, membrane transport, glycogen metabolism, and cell division. Since CBP binds to phosphorylated CREB to promote transcriptional activity, phosphatase-related genes are also thought to be involved in CREB's transcriptional activity. It is highly probable that phosphatase-related genes act on the dephosphorylation of CREB to suppress its transcriptional activity. Therefore, increased CREB's transcriptional activity is suggested to have an ameliorative effect on memory and nerve degeneration.

Protein phosphatase-1 (PP-1), a typical Ser/Thr phosphatase, is known as a major down regulator of CREB activity due to cAMP stimulation (Hagiwara, M. et al., Cell 70:105-113 (1992)). PP-1 activity was reported to be inhibited by phosphorylated Inhibitor-1 (I-1) (Cohen, P., Annu. Rev. Biochem. 58:453-508 (1989)). This report suggested that cellular cAMP response may be amplified by blocking CREB dephosphorylation. However, other than PP-1, phosphatases that down-regulate CREB activity due to cAMP stimulation are not presently known.

DISCLOSURE OF THE INVENTION

The objective of the present invention is to identify phosphatases that suppress transcriptional activity of CREB, and to provide methods of evaluating compounds that regulate phosphatase activities. Compounds inhibiting the activity of phosphatases which suppress CREB's transcriptional activity can ameliorate memory disorders or neurodegeneration by increasing CREB's transcriptional activity. These compounds can thus be expected to be therapeutically effective against a wide variety of neural disorders.

A further objective of the present invention is to identify proteins that enhance cell damage, and to provide methods of evaluating compounds that regulate the activity of these proteins. By regulating the activity of enhancing cell damage, various diseases caused by a variety of cell damages can be treated and prevented.

The present inventors searched various cDNA libraries to identify phosphatases that inhibit CREB's transcriptional activity, and selected phosphatase-related genes using bioinformatics. The effect of inhibiting increased CREB's transcriptional activity using forskolin was also confirmed in selected candidate genes. As a result, two genes encoding proteins comprising phosphatase activity were identified. In addition, the present inventors discovered that compounds that regulate phosphatase activity can be evaluated using the proteins encoded by these genes, thus completing this invention. The present inventors demonstrated that the proteins newly found to have phosphatase activities enhance cell damage. Furthermore, the present invention was completed by discovering that the activity of regulating enhancement of cell damage can be evaluated using these proteins. Specifically, the present invention relates to the following methods of evaluation, and to the uses of phosphatase activity or the activity of enhancing cell damage, which were discovered by the present inventors.

[1] A method for detecting the activity of a test compound to inhibit a dephosphorylation reaction of CREB, wherein the method comprises the steps of:
  (1) contacting a test compound with a protein of any one of the following (a) to (d) under conditions where CREB phosphorylation is possible, or in the presence of phosphorylated CREB or a peptide comprising a CREB phosphorylated site:
    (a) a protein comprising the amino acid sequence of SEQ ID NO: 2 or SEQ ID NO: 4;
    (b) a protein that is functionally equivalent to the protein of (a) and which is encoded by a DNA that hybridizes under stringent conditions with a DNA comprising the nucleotide sequence of SEQ ID NO: 1 or SEQ ID NO: 3;
    (c) a protein comprising the amino acid sequence of SEQ ID NO: 2 or SEQ ID NO: 4, wherein one or more amino acids of the sequence have been substituted, deleted, inserted, and/or added, and where the protein is functionally equivalent to the protein of (a);
    (d) a protein comprising an amino acid sequence with 90% or higher homology to the amino acid sequence of SEQ ID NO: 2 or SEQ ID NO: 4, wherein the protein is functionally equivalent to the protein of (a); and
  (2) measuring the phosphorylation level of CREB or the phosphorylation level of the peptide comprising CREB phosphorylated site.

[2] The method of [1], wherein the CREB phosphorylation level is measured using as an index the transcriptional activity of a CREB-regulated gene.

[3] A method of evaluating a compound comprising the activity of inhibiting a dephosphorylation reaction of CREB, wherein the method comprises the steps of:
  (1) using the method of [1] to detect the activity of a test compound in inhibiting the CREB dephosphorylation reaction; and
  (2) selecting a test compound comprising a high phosphorylation level compared to the CREB phosphorylation level in the absence of the test compound.

[4] A kit for detecting the activity of a test compound in inhibiting a dephosphorylation reaction of CREB, wherein the kit comprises the following components:
  (1) a protein of any one of the aforementioned (a) to (d); and
  (2) a means for measuring the CREB phosphorylation level.

[5] An agent for inhibiting a dephosphorylation reaction of CREB, wherein the agent comprises a compound selected using the method of [3] as an active ingredient.

[6] A therapeutic agent for a mental disorder and/or neurodegenerative disorder, wherein the agent comprises a compound selected using the method of [3] as an active ingredient.

[7] A model animal whose CREB phosphorylation status has been regulated, wherein the animal comprises a transgenic non-human animal whose expression of a protein of any one of the aforementioned (a) to (d) has been regulated.

[8] A method of dephosphorylating CREB, wherein the method comprises the step of contacting CREB with a protein of any one of the aforementioned (a) to (d).

[9] A CREB-dephosphorylating agent, wherein the agent comprises a protein of any one of the aforementioned (a) to (d) as a main ingredient.

[10] An agent for inhibiting a dephosphorylation reaction of CREB, wherein the agent comprises a protein comprising the amino acid sequence of SEQ ID NO: 2 or SEQ ID NO: 4, wherein one or more amino acids of the sequence have been substituted, deleted, inserted, and/or added, and wherein the protein comprises dominant negative characteristic against the protein comprising the amino acid sequence of SEQ ID NO: 2 or SEQ ID NO: 4, or a gene encoding the protein.

[11] A therapeutic agent for a memory disorder and/or neurodegenerative disorder, wherein the agent comprises a protein comprising the amino acid sequence of SEQ ID NO: 2 or SEQ ID NO: 4, wherein one or more amino acids of the sequence have been substituted, deleted, inserted, and/or added, and wherein the protein comprises dominant negative characteristic against the protein comprising the amino acid sequence of SEQ ID NO: 2 or SEQ ID NO: 4, or a gene encoding the protein.

[12] An agent for inhibiting a dephosphorylation reaction of CREB, wherein the agent comprises an antisense nucleotide, which comprises a sequence complementary to the nucleotide sequence of SEQ ID NO: 1 or SEQ ID NO: 3, and which inhibits the expression of a gene comprising the nucleotide sequence of SEQ ID NO: 1 or SEQ ID NO: 3.

[13] A therapeutic agent for a memory disorder and/or neurodegenerative disorder, wherein the agent comprises an antisense nucleotide, which comprises a sequence complementary to the nucleotide sequence of SEQ ID NO: 1 or SEQ ID NO: 3, and which inhibits the expression of a gene comprising the nucleotide sequence of SEQ ID NO: 1 or SEQ ID NO: 3.

[14] An agent for inhibiting a dephosphorylation reaction of CREB, wherein the agent comprises an antibody against a protein of any one of the aforementioned (a) to (d) as a main ingredient.

[15] A therapeutic agent for a memory disorder and/or neurodegenerative disorder, wherein the agent comprises an antibody against a protein of any one of the aforementioned (a) to (d) as a main ingredient.

[16] A method of detecting the activity of a test compound to regulate a cell-damaging effect, wherein the method comprises the steps of:
  (1) under cell-damaging conditions, contacting a test compound with cells expressing a protein of any one of the aforementioned (a) to (d):
  (2) comparing the cell-damaging level of the cells to that of the control; and
  (3) associating the difference in cell-damaging level compared to the control with the activity of the test compound to regulate the cell damaging effect.

[17] The method of [16], wherein the cell-damaging conditions are provided by administration of a compound comprising a cell-damaging effect.

[18] The method of [17], wherein the compound comprising a cell-damaging effect is an apoptosis-inducing agent.

[19] The method of [18], wherein the apoptosis-inducing agent is an endoplasmic reticulum calcium pump inhibitor.

[20] The method of [16], wherein the test compound's effect in suppressing the cell-damaging effect is detected when the cell damage level is low compared to that of the control.

[21] A method of selecting a test compound comprising the activity of regulating a cell-damaging effect, wherein the method comprises the steps of:

(1) detecting the activity of the test compound in regulating the cell-damaging effect using the method of [16]; and (2) selecting a test compound which has a different cell-damaging level compared to that of the control.

[22] The method of [21], wherein the method comprises the step of selecting a test compound with a reduced cell-damaging level compared to the control.

[23] The method of [22], wherein the test compound is a compound selected using the method of [3].

[24] An agent for regulating a cell-damaging effect, wherein the agent comprises a compound selected using the method of [21] as an active ingredient.

[25] The agent for regulating a cell-damaging effect according to

[24], wherein the cell is a neuron.

[26] An agent for suppressing a cell-damaging effect, wherein the agent comprises a compound selected using the method of [22] as an active ingredient.

[27] The agent for suppressing a cell-damaging effect according to

[26], wherein the cell is a neuron.

[28] A therapeutic agent for a mental disorder and/or neurodegenerative disorder, wherein the agent comprises a compound selected using the method of [22] as an active ingredient.

[29] An agent for enhancing a component comprising a cell-damaging effect, wherein the agent comprises a protein of any one of the aforementioned (a) to (d), or a polynucleotide encoding the protein as an active ingredient.

[30] The enhancing agent of [29], wherein the component comprising a cell-damaging effect is an apoptosis-inducing agent.

[31] The enhancing agent of [30], wherein the apoptosis-inducing agent is an antitumor agent.

[32] A method of enhancing a component comprising a cell-damaging effect, wherein the method comprises the step of administering a protein of any one of the aforementioned (a) to (d), or a polynucleotide encoding the protein.

[33] A cell-damaging composition comprising the following components:

(1) a protein of any one of the aforementioned (a) to (d), or a polynucleotide encoding the protein; and (2) a component comprising cell-damaging effect.

[34] The cell-damaging composition of [33], wherein the cell is a tumor cell.

The present invention concerns methods for detecting the activity of inhibiting the activity of phosphatases encoded by the following two genes, or proteins functionally equivalent to these phosphatases, and methods of evaluation using these detection methods. Alternatively, the present invention concerns methods of detecting the activity of regulating the cell-damaging-enhancing effect comprised by proteins encoded by the following two genes, or proteins functionally equivalent to these proteins, and methods of screening using these methods.

|  | Nucleotide sequence | Amino acid sequence |
|---|---|---|
| OVARC1000473 | SEQ ID NO: 1 | SEQ ID NO: 2 |
| NT2RM1000377 | SEQ ID NO: 3 | SEQ ID NO: 4 |

The two genes mentioned above were both discovered from within a full-length cDNA database (EP1074617) of the Helix Research Institute. Whilst the full-length cDNA structures of these genes were known, their phosphatase activity towards CREB was unknown.

OVARC1000473 (GenBank BC004176) is a gene isolated from the ovary. Of the total of 218 amino acid residues encoded by this gene, the C-terminal amino acids (122-218) have 34% homology to a dual specific phosphatase (Swissplot Q16690), and a phosphatase catalytic site has been recognized in the sequence from amino acid numbers 159 to 176 (Keyse S. M., Biochem. Biophys. Acta (1995, Mar 16) 1265 (2-3):152-60) (FIG. 1, upper panel).

NT2RM1000377 (GeneBank AK022513) is a gene isolated from human neuroblast NT2 cells. The amino acid sequence encoded on this gene (140 amino acid residues) matches the C-terminal amino acid residues 343-482 of dual specific protein phosphatase MKP-5 (GenBank AB026436) and possesses a phosphatase catalytic site at residues 67 to 78 of the amino acid sequence (FIG. 1, bottom panel). In that amino acid sequence, a region with high amino acid primary sequence homology to Cdc25 was found. This region is indicated in FIG. 1 (bottom) as the Cdc25-like domain. CDC25A (cell division cycle 25A, M-phase inducer phosphatase 1) is a type of tyrosine protein phosphatase that takes on a function necessary for cell cycle progression. It is known to dephosphorylate the CDC2 protein to increase the kinase activity. The nucleotide sequence of MKP-5 and the amino acid sequence encoded by this nucleotide sequence are shown in SEQ ID NO: 5 and SEQ ID NO: 6, respectively. This gene is also registered in the database as dual specificity phosphatase 10 (DUSP10) (GenBank NM_144729, GenBank NM_144728).

These genes were identified as follows: First, phosphatase-related genes were selected from the Helix Research Institute cDNA database using the BLAST algorithm. Next, the selected candidate genes were transfected into PC12 cells along with a CRE reporter gene. Forskolin was applied to these cells to induce CREB's transcriptional activity. As a result, the two clones mentioned above were identified as genes comprising the effect of suppressing increased CREB's transcriptional activity caused by forskolin.

It was further found that the activity of suppressing CREB dephosphorylation could be evaluated by using these proteins as target molecules. More specifically, the present invention relates to methods of detecting a test compound's activity in inhibiting the CREB dephosphorylation reaction, where the method comprises the steps of:

(1) contacting a test compound with a protein of any one of the aforementioned (a) to (d) underconditions where CREB phosphorylation is possible, or in the presence of phosphorylated CREB or a peptide comprising a CREB phosphorylated site; and (2) measuring the phosphorylation level of CREB or the phosphorylation level of the peptide comprising CREB phosphorylated site.

A method of detecting the activity of inhibiting a CREB dephosphorylation reaction according to this invention is performed in the following manner, using the aforementioned proteins or proteins functionally equivalent to the aforementioned proteins. More specifically, under conditions where CREB phosphorylation is possible, or in the presence of phosphorylated CREB or a peptide comprising that phosphorylation site, a test compound is contacted with the aforementioned protein's or proteins functionally equivalent to the aforementioned proteins; and the phosphorylation level of CREB and/or the peptide comprising the phosphorylation site is measured. Such measurements can be performed in vivo or in vitro.

Phosphatases used in this invention, which suppress CREB's transcriptional activity, are proteins comprising all or a portion of a sequence shown in SEQ ID NO: 2 or SEQ ID NO: 4, or proteins that are functionally equivalent to these proteins.

Herein, "functionally equivalent" means that the proteins of interest comprise the activity of suppressing the increase of CREB's transcriptional activity induced by forskolin, or comprise the activity of dephosphorylating CREB. More specifically, the "proteins that are functionally equivalent" of this invention include fragments that may catalyze the dephosphorylation reaction. This activity can be confirmed by contacting CREB with the proteins under conditions allowing CREB phosphorylation, and using the decrease of CREB phosphorylation level as an indicator.

For example, if a protein suppresses expression of the CRE reporter gene in the presence of CREB and cAMP, that protein can be referred to as a functionally equivalent protein. More specifically, the activity of a target protein in suppressing CREB transcriptional activation can be determined by:

(1) preparing a vector for expressing a gene encoding a target protein;
(2) transfecting the expression vector into a cell together with the CRE reporter gene;
(3) adding forskolin; and
(4) confirming expression of the CRE reporter gene.

Furthermore, an above-mentioned protein in which phosphatase activity was discovered in this invention was demonstrated to comprise not only phosphatase activity, but also the activity of enhancing cell damage. It was found that by using such a protein as a target molecule, the activity of regulating enhancement of cell-damaging effect could be evaluated. More specifically, the present invention provides methods of detecting the activity of regulating enhancement of cell-damaging effect, where the methods comprise the steps of:

(1) under cell-damaging conditions, contacting a test compound with cells expressing a protein of any one of the aforementioned (a) to (d):
(2) comparing the cell-damaging level of the cells to that of the control; and
(3) associating the difference in cell-damaging level compared to the control with the activity of the test compound to regulate the cell damaging effect.

NT2RM1000377, a phosphatase-related gene elucidated in the present invention, comprises the activity of enhancing cell-damaging effect. Therefore, the effect of regulating its activity can be detected by the method described above. More specifically, when cell-damaging level is low compared to that of a control, the activity of suppressing enhancement of cell-damaging effect is detected. On the other hand, when cell-damaging level is high compared to that of the control, the activity of stimulating enhancement of cell-damaging effect is detected.

In the present invention, the term "cell-damaging conditions" refers to conditions that prevent the growth and survival of cells. Such conditions can be provided, for example, by inducing cell apoptosis. Specifically, cell-damaging conditions that can be used include administering cell-damaging compounds, changing culture conditions to induce cell apoptosis, and such. Apoptosis-inducing agents can be used as cell-damaging compounds. Various compounds that induce cell apoptosis are known. More specifically, fas ligands and endoplasmic reticulum calcium pump inhibitors comprise the effect of inducing cell apoptosis. The timing for administrating cell-injuring compounds is discretionary. More specifically, cell-damaging compounds can be administered before, during, or after contacting a test compound with cells.

It is well-known that, by depleting serum, apoptosis can be induced in cells that require serum or other culture components. The timing for inducing apoptosis by altering culture conditions is also arbitrary. More specifically, changes to culture conditions to induce apoptosis can be carried out before, during or after administration of the test compound. For example, when apoptosis is induced before administering a test compound, the therapeutic effect of that test compound on cell-damaging enhancement can be evaluated. On the other hand, when apoptosis is induced after administering the test compound, the preventive effect of predominantly the test compound on cell-damaging enhancement can be determined.

Cells showing neuron-like characteristics can be designated as cells that can be used in the methods of this invention. All of the proteins used as target molecules in this invention are involved with CREB dephosphorylation. As described above, CREB is strongly related to memory formation and neuronopathy. Therefore, the use of cells showing neuron-like characteristics is preferred in evaluating the effect on these functions. PC12 can be designated as a cell line showing neuron-like characteristics. PC12 is a cell line established from Rattus norvegicus-derived adrenal gland pheochromocytoma. It can be differentiated into neuron-like cells on stimulation by retinoic acid, NGF, and so on. PC12 (ATCC CRL-1721) is obtainable from a cell bank.

In the methods of the present invention, cells to which a test compound is not administered can be used as a control. Furthermore, an experiment without cell-damaging conditions can also be performed to more accurately evaluate test compound activity. By combining these experiments, the influence on cells of the test compound itself can be evaluated at the same time. More specifically, when cell damage is observed regardless of the presence or absence of cell-damaging conditions, the test compound itself is considered to comprise cell-damaging effect.

Methods of measuring cell-damaging level are well known. Specifically, cell-damaging level can be determined by using as an indicator the level of cell growth, the level of cells that have undergone apoptosis, or the level of destroyed cells.

NT2RM1000377, a phosphatase-related gene elucidated by the present invention, was confirmed to enhance cell-damaging effect due to endoplasmic reticulum calcium pump inhibitors. The term "cell-damaging effect" refers to interference with cell survival. For example, apoptosis induction is included in cell damage. Furthermore, the phrase "enhancement of cell damage" refers to an observed further increase in cell-damaging level due to the addition of some other factor, compared to cell-damaging level observed with one factor alone, and where each cell's cell-damaging level is measured using the above-mentioned method.

Therefore, functionally equivalent proteins of this invention include proteins comprising the activity of enhancing cell-damaging effect. Such activity can be confirmed, for example, by the following method: The above-mentioned activity can be evaluated by contacting cells under cell-damaging conditions with a protein whose activity is to be confirmed, and then comparing the cell-damaging level of these cells with the cell-damaging level when the protein was not contacted. The following conditions can be indicated as cell-damaging conditions:

For example, a compound comprising cell-damaging effect can be contacted with cells. If such conditions are applied to cells in which a certain protein has been forcibly expressed, and cell-damaging effect is then enhanced compared to a control, then this protein can be confirmed to comprise the above-mentioned activity.

Polynucleotides encoding the phosphatases used in the present invention can be isolated by the hybridization method, PCR method, and such, by using probes and/or primers produced based on sequence information according to SEQ ID NO: 1 or SEQ ID NO: 3.

These polynucleotides are not limited to those comprising the sequence of SEQ ID NO: 1 or SEQ ID NO: 3, as long as the proteins expressed from the polynucleotides comprise substantially the same function as the aforementioned phosphatases. More specifically, the following are included:

(1) polynucleotides that hybridize to polynucleotides comprising a sequence of the aforementioned SEQ ID NOs, and (2) polynucleotides encoding proteins comprising an amino acid sequence of a protein encoded by an aforementioned polynucleotide, in which one or more (and preferably several) amino acids have been substituted, deleted, and/or added.

Such polynucleotides can be easily obtained by methods such as site-directed mutagenesis ("Current Protocols in Molecular Biology", edit. Ausubel et al. (1987) John Wiley & Sons, Section 8.1-8.5), PCR method ("Current Protocols in Molecular Biology", edit. Ausubel et al. (1987) John Wiley & Sons, Section 6.1-6.4), or conventional hydridization methods ("Current Protocols in Molecular Biology", edit. Ausubel et al. (1987) John Wiley & Sons, Section 6.3-6.4).

One skilled in the art can use a polynucleotide comprising the sequence of SEQ ID NO: 1 or SEQ ID NO: 3, or a portion thereof, as a probe, or use oligonucleotides that specifically hybridize to this polynucleotide as primers, and can thereby isolate polynucleotides that hybridize with this polynucleotide.

Stringent hybridization conditions for encoding functionally equivalent proteins refer to washing conditions that are normally "1×SSC, 37° C." or so. More stringent conditions are "0.5×SSC, 0.1% SDS, 42° C." or so, and even more stringent conditions are "0.1×SSC, 0.1% SDS, 65° C." or so. As conditions for hybridization become more stringent, polynucleotides comprising higher homology to the probe sequence may be isolated. However, the above-mentioned hybridization conditions are examples, and one skilled in the art can accomplish stringencies suited to their purpose by appropriately selecting probe concentration, probe length, reaction time, reaction temperature, reagent concentration, and so on, depending on conditions such as the nucleotide sequence to be used and the type of gene pool.

Proteins encoded by the polynucleotides isolated by methods such as those described above normally have amino acid sequences highly homologous to phosphatases comprising the amino acid sequence of SEQ ID NO: 2 or SEQ ID NO: 4. "High homology" refers to sequence homology of at least 50% or more, more preferably 70% or more, and even more preferably 90% or more (for example, 95% or more).

Homology of amino acid sequences and nucleotide sequences can be determined using the Gapped BLAST algorithm of Altshul et al. (Nucleic Acids Res. 25:3389-3402 (1997)). Programs such as BLASTN and BLASTX have been developed based on this algorithm. When a nucleotide sequence database is the object of BLASTN program analysis, parameters can be set, for example, at except=10 and wordlength=11. Furthermore, when an amino acid sequence database is analyzed with BLASTX, the parameters can be set, for example, at except=10 and wordlength=3. When using the various BLAST programs, the default parameters for each program may be used. One can refer to the homepage of the National Center for Biotechnology Information (NCBI) (http://www.ncbi.nlm.nih.gov) or the like for the specific procedures for these analysis methods.

The amino acid sequences of SEQ ID NO: 2 and SEQ ID NO: 4 are encoded by the nucleotide sequences of SEQ ID NO: 1 and SEQ ID NO: 3, respectively. Proteins comprising these amino acid sequences comprise the activity of dephosphorylating CREB, and regulate any increase of CREB's transcriptional activity. Proteins that comprise activities functionally equivalent to those of these proteins can be used for the methods of this invention.

Functionally equivalent proteins also include proteins produced using methods for introducing mutations to protein amino acid sequences, such as site-directed mutagenesis. The number of amino acid mutations and mutation sites in the proteins are not particularly limited as long as their functions are maintained. The number of mutations is typically 10% of the total amino acids or less, preferably 5% of the total amino acids or less, and even more preferably 1% of the total amino acids or less. In terms of maintaining protein function, the amino acids to be replaced are preferably amino acids with properties similar to those of the amino acid prior to replacement. For example, since Ala, Val, Leu, Ile, Pro, Met, Phe, and Trp are all categorized as non-polar amino acids, they are considered to possess similar properties. Examples of uncharged amino acids are Gly, Ser, Thr, Cys, Tyr, Asn, and Gln. Furthermore, examples of acidic amino acids are Asp and Glu. Examples of basic amino acids are Lys, Arg, and His.

Genes encoding functionally equivalent proteins can be obtained from different tissues and animals by using hybridization technology, PCR method, and such, thus yielding proteins of different origins. Organisms for use in isolating functionally equivalent proteins are not particularly limited. Examples include mammals such as humans, mice, rats, rabbits, monkeys, pigs, and cows.

A protein that, through some process (such as cleavage or modification), produces a protein which comprises the activity of suppressing an increase of CREB's transcriptional activity or the activity of enhancing cell-damaging effect can also be used in the present invention, even when the target protein itself does not comprise such activity. Furthermore, since the entire amino acid structure is not normally essential for a protein's activity, a partial peptide of the aforementioned protein may also be used. More specifically, partial peptides that maintain a portion necessary for displaying an activity functionally equivalent to that of the aforementioned protein may be used in the present invention. Partial peptides can be produced by genetic engineering methods, peptide synthesis methods, or by cleavage using an appropriate enzyme, such as a peptidase.

Proteins required for the present invention can be obtained, for example, by expression from a transformant that has been transformed with an expression vector comprising the sequence of SEQ ID NO: 1 or SEQ ID NO: 3. The expressed proteins can be purified and isolated from the culture solution or cell fraction using conventional methods.

Examples of methods of purification and isolation include the following methods: First, the cells or supernatant are recovered by methods such as filtration and centrifugation. When proteins are expressed in cells, the cell wall and/or cell membrane need to be disrupted using physical techniques such as ultrasonication or milling, or by using lysozymes or the like. The protein of interest can be isolated and purified by treating the thus-obtained solution, which contains the protein of the present invention, with an appropriate combination of common techniques such as dialysis, column chromatography (ion exchange, affinity, etc.), and gel filtration.

When producing a protein using genetic engineering methods, a sequence encoding a polypeptide with affinity can be added to the terminus of a gene encoding the target protein, and then expressed. The affinity of the added polypeptide can be used to purify the target protein. Polypeptides with affinity towards metal ion chelates, biotins, streptavidin, antibodies, and such are known. For example, if basic amino acids, such as histidine, lysine, and arginine, are added to the target protein, the protein can be easily purified using affinity towards metal ions.

The purified protein can be used as a CREB dephosphorylation agent. CREB dephosphorylation agents can be used to evaluate compounds that regulate the dephosphorylation of CREB. Furthermore, compounds that comprise the activity of inhibiting dephosphorylation, and which can be discovered by an evaluation method utilizing a CREB dephosphorylation agent, can be used as therapeutic or preventive agents for memory disorders and/or neurodegenerative disorders.

Alternatively, proteins obtained in this manner can be used as cell-damaging-enhancing agents. Cell-damaging-enhancing agents of this invention can be used for evaluating the activity of regulating cell-damaging enhancement. Compounds comprising this activity are useful for regulating cell-damaging enhancement.

Furthermore, the cell-damaging-enhancing agents of this invention are useful, for example, for enhancing the effect of compounds comprising cell-damaging effect, such as antitumor agents. Specifically, apoptosis-inducing agents can be indicated as compounds comprising cell-damaging effect. Apoptosis-inducing agents include endoplasmic reticulum calcium pump inhibitors. For example, thapsigargin, a sarcoplasmic reticulum calcium pump inhibitor, is a representative compound comprising cell-damaging effect, and has been researched with the aim of treating cancer. The cell-damaging-enhancing agent of this invention can be administered separately from compounds comprising cell-damaging effect. Alternatively, the enhancing agent of this invention can be premixed with compounds comprising cell-damaging effect to produce a composition in which the effect is enhanced. Furthermore, polynucleotides encoding the aforementioned protein are included in the cell-damaging-enhancing agents of this invention. These polynucleotides can express proteins that enhance cell-damaging effect in a living body after administration, and can thus accomplish the intended effect. Techniques for expressing a target protein by transferring genes into a living body are well known.

Furthermore, NT2RM1000377 of the present invention was found through analysis to be a type of splicing variant of dual specific protein phosphatase MKP-5. Therefore, MKP-5 also comprises a function similar to that of NT2RM1000377, and can be used as a dephosphorylation agent. Furthermore, in a manner similar to NT2RM1000377, MKP-5 can be used for methods of detecting the activity of test compounds that inhibit the CREB dephosphorylation reaction, methods of evaluating compounds comprising the activity of inhibiting the CREB dephosphorylation reaction, and methods of CREB dephosphorylation. Compounds comprising the activity of inhibiting CREB dephosphorylation, discovered using MKP-5, can be used as therapeutic or preventive agents against memory disorders and/or neurodegenerative disorders. The present inventors discovered this new finding that MKP-5 comprises CREB dephosphorylation effect.

More specifically, the present invention relates to a method for detecting the activity of a test compound to inhibit a dephosphorylation reaction of CREB, wherein the method comprises the steps of:

(1) contacting a test compound with a protein of any one of the following (a) to (d) under conditions where CREB phosphorylation is possible, or in the presence of phosphorylated CREB or a peptide comprising a CREB phosphorylated site:
   (a) a protein comprising the amino acid sequence of SEQ ID NO: 6;
   (b) a protein that is functionally equivalent to the protein of (a) and which is encoded by a DNA that hybridizes under stringent conditions with a DNA comprising the nucleotide sequence of SEQ ID NO: 5;
   (c) a protein comprising the amino acid sequence of SEQ ID NO: 6, wherein one or more amino acids of the sequence have been substituted, deleted, inserted, and/or added, and where the protein is functionally equivalent to the protein of (a);
   (d) a protein comprising an amino acid sequence with 90% or higher homology to the amino acid sequence of SEQ ID NO: 6, wherein the protein is functionally equivalent to the protein of (a); and
(2) measuring the phosphorylation level of CREB or the phosphorylation level of the peptide comprising CREB phosphorylated site.

Furthermore, the present invention relates to a method of evaluating a compound comprising the activity of inhibiting a dephosphorylation reaction of CREB, wherein the method comprises the steps of:
(1) using the aforementioned method to detect the activity of a test compound in inhibiting the CREB dephosphorylation reaction; and
(2) selecting a test compound comprising a high phosphorylation level compared to the CREB phosphorylation level in the absence of the test compound.

Furthermore, the present invention relates to agents that inhibit the CREB dephosphorylation reaction, agents that suppress the enhancement of cell-damaging effect, or therapeutic agents for memory disorders and/or neurodegenerative disorders, where these agents comprise a compound selected by these evaluation methods as an active ingredient. Furthermore, the present invention relates to methods of treating memory disorders and/or neurodegenerative disorders, in which the methods comprise the step of administering a compound selected by these evaluation methods. Alternatively, the present invention relates to the use of compounds selected by these evaluation methods for the production of therapeutic agents for memory disorders and/or neurodegenerative disorders.

Furthermore, the present invention relates to a kit for detecting the activity of a test compound in inhibiting a dephosphorylation reaction of CREB, wherein the kit comprises the following components:
(1) a protein of any one of the aforementioned (a) to (d):
(2) a means for measuring the CREB phosphorylation level.

Alternatively, the present invention relates to a kit for detecting the activity of a test compound in regulating enhancement of cell-damaging effect, where the kit comprises the following components:
(1) cells expressing a protein of any one of the aforementioned (a) to (d); and
(2) a compound comprising cell-damaging effect against the aforementioned cells.

Additional components can be combined in the kits of this invention, depending on purpose. For example, compounds clearly comprising (or not comprising) the activity of interest can be included as a negative or positive control. Furthermore, a medium and a culturing vessel for culturing cells can be included in a kit where cell culture is required. Furthermore, components for evaluating cell-damaging level can be included in a kit where evaluation of cell-damaging effect is required. For example, the cell-damaging level of PC12 neurons can be evaluated by using LDH in the culture supernatant as an indicator. Therefore, a reagent for measuring LDH activity can be included in a kit.

Furthermore, the present invention relates to model animals whose CREB phosphorylation state is regulated, where these animals are transgenic non-human animals with regulated expression of a protein of any one of the aforementioned (a) to (d).

In addition, the present invention relates to methods of CREB dephosphorylation, where the methods comprise the step of contacting CREB with a protein of any one of (a) to (d). Alternatively, the present invention relates to CREB dephosphorylation reagents comprising a protein of any one of (a) to (d) as the main ingredient. Furthermore, the present invention relates to the use of a protein of any one of (a) to (d) in the production of a CREB dephosphorylating agent.

In addition, the present invention relates to:
agents that inhibit the CREB dephosphorylation reaction,
agents that enhance cell-damaging effect,
or therapeutic agents for memory disorders and/or neurodegenerative disorders, where the agents comprise:
a protein comprising the amino acid sequence of SEQ ID NO: 6, in which one or more amino acids of the sequence have been substituted, deleted, inserted, and/or added, and where the protein comprises dominant negative character towards a protein comprising the amino acid sequence of SEQ ID NO: 6, or a gene encoding this protein.

Furthermore, the present invention relates to agents inhibiting the CREB dephosphorylation reaction, agents suppressing enhancement of cell-damaging effect, or therapeutic agents for memory disorders and/or neurodegenerative disorders, where the agents comprise an antisense nucleotide which comprises a sequence complementary to the nucleotide sequence of SEQ ID NO: 5, and which inhibits the expression of a gene comprising the nucleotide sequence of SEQ ID NO: 5. In addition, the present invention relates to agents that inhibit the CREB dephosphorylation reaction, agents that suppress enhancement of cell-damaging effect, or therapeutic agents for memory disorders and/or neurodegenerative disorders, where the agents comprise an antibody against a protein of any one of (a) to (d) as the main ingredient.

When expressing proteins used in this invention using genetic engineering techniques, an expression vector must be selected appropriate to the type of host cell to be used. The host cells for expressing proteins used in this invention are not limited. Specifically, examples of host cells include prokaryotic cells, such as *Escherichia coil* and *Bacillus subtilis*, as well as eukaryotic cells, such as yeast, insect cells, and animal cells, such as amphibian cells and mammalian cells.

Normally, when using prokaryotes, an expression vector comprising a promoter, an initiation codon, a sequence encoding the target protein, a stop codon, and a self-replicating unit is used. When using eukaryotic cells as hosts, it is preferable to use an expression vector comprising a promoter, an initiation codon, a sequence encoding the target protein, and a stop codon. As necessary, an enhancer sequence, 5' and 3' non-coding regions of the target protein, a polyadenylation site, and a self-replicable unit can be inserted.

When bacteria are used as hosts, the term "promoter" refers a promoter-operator region comprising a promoter, an operator, and the Shine-Dalgarno (SD) sequence. Examples of an appropriate promoter include lactose operon, PL promoter, and tryptophan promoter. An example of a promoter when yeast is used as a host is the pho5 promoter. Examples of promoters that may be used for expression using mammalian cells include the HTLV-LTR promoter, SV40 early and late promoters, CMV promoter, and mouse metallothionein promoter. Manipulations required for DNA cloning, plasmid construction, host transformation, culturing of that host, collection of protein from the culture, and such, which are necessary for carrying out the present invention, can be performed according to methods well known to one skilled in the art ("Molecular Cloning 2nd. Edition", T. Maniatis et al., Cold Spring Harbor Laboratory (1989); "Molecular Cloning 3rd. Edition", T. Maniatis et al., Cold Spring Harbor Laboratory (2001); and "DNA Cloning", D. M. Glover, IRL Press (1985), etc.).

Expression vectors can be transfected into host cells according to known methods such as calcium phosphate precipitation, pulse electroporation (Current Protocols in Molecular Biology, Ausubel et al. (1987) John Wiley & Sons, Section 9.1-9.9), lipofectamine method (GIBCO-BRL), and microinjection.

In the present invention, CREB phosphorylation level can be evaluated, for example, by observing the expression level of the CRE reporter gene in the presence of CREB, cAMP, and an aforementioned protein. For example, a gene encoding an aforementioned protein is inserted into an expression vector, and is transferred into cells along with the CRE reporter gene. The activity of inhibiting the CREB dephosphorylation reaction can be detected by, in the presence of a test compound, inducing cAMP in cells by adding compounds such as forskolin, and then confirming expression of the CRE reporter gene.

When expressing a gene encoding the aforementioned protein and the CRE reporter gene in vivo, the following expression vectors may be used: Animal cells that express CREB, but do not express the gene encoding the aforementioned protein, or that lack this gene, can be used as host cells. Examples of such cells include PC12 cells, Jurkat cells, primary culture neurons, and neuroblastoma (SH-SY5Y, IMR32, Neuro2a).

Herein, a CRE reporter gene refers to a gene in which the CRE region and a reporter gene are linked. The CRE region is a portion essential to induction by cAMP in the transcription regulatory site of a gene cluster with cAMP-promoted expression. Somatostatin, c-fos, and such are known as gene clusters whose expressions are cAMP-promoted. Their nucleotide sequences have a palindromic structure such as the eight nucleotide structure TGACGTTCA or similar. Examples of reporter genes include genes encoding luciferase, catalase, β-galactosidase, Green Fluorescent Protein (GFP), and such.

The activity of the aforementioned protein in inhibiting dephosphorylation can also be measured in vitro. For example, the activity can be measured by incubating the aforementioned protein with phosphorylated CREB in the presence of a test compound, and then measuring the change in CREB phosphorylation level. Change in CREB phosphorylation level can be measured, for example, using antibodies that can distinguish CREB phosphorylation levels.

CREB's amino acid sequence is known (GenBank No. M27691). Based on this sequence information, CREB can be readily obtained by those skilled in the art using conventional methods (for example, hybridization technology, PCR methods, and genetic engineering methods such as those illustrated in the method of obtaining proteins used for this invention). Furthermore, CREB phosphorylation can be performed according to the following method: Cell supernatant is removed and then washed with PBS or the like, and the protein is solubilized using a solubilizing buffer (10 mM Tris-HCl at pH 7.4, 1% Triton X-10.0, 1% SDS, 0.2 mM sodium vanadate, 10 mM sodium fluoride, 1 mM EDTA, 1 mM PMSF, 2 µg/mL leupeptin, 2 µg/mL aprotinin). Next, the sample is separated without denaturing by using SDS-PAGE electrophoresis. After electrophoresis, the electrophoresed sample is transferred to a PVDF filter, and identified with an anti-phosphorylation CREB antibody (Beitner-Johnson D. et al. J. Biol. Chem. (1998, Jul. 31) 273 (31):19834-9).

Methods for producing antibodies that can discern protein phosphorylation levels are well known. For example, the serine at position 133 of CREB is phosphorylated. Thus, using phosphorylated serines, an oligopeptide with an amino acid sequence comprising the serine 133 is synthesized, and by using this as an immunogen, antibodies that can differentiate CREB phosphorylation levels can be obtained. Furthermore, antibodies against phosphorylated CREB are commercially available. For example, #9191S is an antibody against phosphorylated CREB available from NEW ENGLAND BIOLAB Inc.

Components necessary to the method of detecting the aforementioned proteins' activity in inhibiting dephosphorylation can be pre-combined in kits. More specifically, the present invention relates to kits for detecting a test compound's activity in inhibiting a CREB dephosphorylation reaction due to the aforementioned protein, where the kits comprise the following components:
  (1) a protein of the aforementioned (a) to (d); and
  (2) a means for measuring the CREB phosphorylation level.

CREB and/or a peptide comprising an amino acid sequence comprising a CREB phosphorylation site can be further combined in the kits of this invention. The CREB and/or peptide comprising an amino acid sequence comprising a CREB phosphorylation site, which are composed into the kits of this invention, are used in the aforementioned detection methods under pre-phosphorylated conditions, or conditions where phosphorylation is possible. Components required to provide conditions where phosphorylation is possible can also be added to the kits.

Specifically, when expressing CREB in cells, CREB phosphorylation is accomplished by cAMP's action on cells. Therefore, CREB-producing cells, media for culturing these cells, and cAMP can be kit components. Alternatively, a peptide that comprises phosphorylated CREB or an amino acid sequence comprising a CREB phosphorylation site may also be a component.

In the kits of this invention, the means for measuring the level of CREB phosphorylation can be, for example, the aforementioned CRE reporter gene expression system, and antibodies that can differentiate CREB phosphorylation levels.

Control samples providing positive or negative results, and instructions can be combined in the kits of this invention. The kits of this invention are useful for the following evaluation methods. When performing the following evaluation methods using the kits of this invention, the test compounds to be evaluated can also be combined.

The present invention relates to evaluation methods in which the above-mentioned detection methods are applied. The evaluation methods of this invention comprise the steps of:
  (1) using the aforementioned method to detect the activity of a test compound in inhibiting the CREB dephosphorylation reaction; and
  (2) selecting a test compound comprising a high phosphorylation level compared to the CREB phosphorylation level in the absence of the test compound.

Examples of test compounds used for evaluation in this invention include cell extracts, gene library expression products, synthetic low-molecular weight compounds, synthetic peptides, natural compounds, and synthetic compounds produced by conventional combinatorial chemistry techniques. The test compounds further include high molecular compounds, such as dominant negative forms, antisense nucleotides, and antibodies. These test compounds are only examples, and the test compounds are not limited thereto.

Furthermore, compounds comprising the activity of regulating enhancement of cell-damaging effect can be selected using this invention's methods. More specifically, the present invention relates to methods for selecting compounds comprising the activity of regulating cell-damaging effect, where the methods comprise the steps of:
  (1) detecting the activity of the test compound in regulating the cell-damaging effect using the aforementioned methods; and
  (2) selecting a test compound which has a different cell-damaging level compared to that of the control.

The compounds selected by the present invention comprise the effect of regulating enhancement of cell-damaging effect. The activity of regulating the enhancement of cell-damaging effect includes suppression and stimulation of enhancement. Compounds comprising the activity of suppressing enhancement of cell-damaging effect suppress the enhancement of the cell-damaging effect of the proteins encoded by OVARC1000473 (SEQ ID NO: 1) and NT2RM1000377 (SEQ ID NO: 3).

Compounds, such as those mentioned previously in the methods for evaluating the activity of regulating phosphatase activity, can be used as test compounds in the methods of the present invention. Furthermore, compounds found using the above methods to comprise the effect of inhibiting the dephosphorylation reaction can be used as test compounds when carrying out the methods for evaluating the activity of regulating enhancement of cell damage, based on this invention. Compounds selected in this manner are compounds that comprise both the effect of inhibiting dephosphorylation and suppressing the enhancement of cell damage. Such compounds are useful for the treatment of disorders, such as neuronopathy, that are caused by various cell damages.

Enhanced cell-damaging effect forms the pathology of disorders such as neuronopathy, which are caused by various cell damages. Therefore, compounds that can suppress the enhancement of cell-damaging effect are useful for the treatment and prevention of these disorders.

In the present invention, proteins comprising the amino acid sequence of SEQ ID NO: 2 or SEQ ID NO: 4 were found to comprise the effects of CREB dephosphorylation and cell-damaging enhancement. Therefore, by suppressing the activity or expression of these proteins, the CREB dephosphorylation reaction or cell-damaging enhancement in a living body can be regulated. To regulate the activity and expression of these proteins, for example, dominant negative forms and antisense nucleotides can be used.

More specifically, the present invention relates to agents that inhibit a CREB dephosphorylation reaction, agents that suppress enhancement, or therapeutic agents for memory disorders and/or neurodegenerative disorders, where the agents comprise a protein comprising the amino acid sequence of SEQ ID NO: 2 or SEQ ID NO: 4, in which one or more amino acids of the sequence have been substituted, deleted, inserted, and/or added, and in which the protein comprises dominant negative characteristic against a protein comprising the amino acid sequence of SEQ ID NO: 2 or SEQ ID NO: 4, or a gene encoding this protein.

Furthermore, the present invention relates to agents that inhibit a CREB dephosphorylation reaction, agents that suppress cell-damaging enhancement, or therapeutic agents for memory disorders and/or neurodegenerative disorders, where the agents comprise an antisense nucleotide which comprises a sequence complementary to the nucleotide sequence of SEQ ID NO: 1 or SEQ ID NO: 3, and inhibits the expression of a gene comprising the nucleotide sequence of SEQ ID NO: 1 or SEQ ID NO: 3.

Herein, a dominant negative form refers to a protein comprising dominant negative characteristic against a protein comprising the amino acid sequence of SEQ ID NO: 2 or SEQ ID NO: 4. Such dominant negative forms have the function of eliminating or decreasing the activity of an endogenous wild type protein originally in cells. For example, an inactive form, whose CREB dephosphorylation activity and/or cell-damaging enhancing activity is low or absent, can be obtained by altering an amino acid sequence in SEQ ID NO: 2 or SEQ ID NO: 4, wherein the altered amino acid sequence corresponds to a sequence considered to affect the activity of a protein encoded by the amino acid sequence of SEQ ID NO: 2 or SEQ ID NO: 4.

CREB dephosphorylation and/or cell-damaging enhancement can be suppressed using the dominant-negative effect (antagonistic inhibition of the inactive form) by administering this kind of dominant-negative form to cells, or by expressing in cells genes which encode the dominant negative form. Therefore, dominant negative forms of this invention, or genes encoding a dominant negative form, can be used as agents for inhibiting a CREB dephosphorylation reaction, agents for suppressing enhancement of cell-damaging effect, or as therapeutic or preventive agents for memory disorders and/or neurodegenerative disorders.

The antisense nucleotides of this invention refer to polynucleotides that suppress the expression of a protein that comprises the amino acid sequence of SEQ ID NO: 2 or SEQ ID NO: 4. Specifically, antisense nucleotides comprising such activity suppress CREB dephosphorylation and/or cell-damaging enhancement, and therefore can be used as agents to inhibit a CREB dephosphorylation reaction, agents to suppress enhancement of cell-damaging effect, or as therapeutic or preventive agents for memory disorders and/or neurodegenerative disorders.

Antisense nucleotides may be antisense DNAs or antisense oligonucleotides. Antisense DNAs preferably have a chain length of several dozen base pairs or more. The antisense DNAs can be used alone or by insertion in the antisense direction into appropriate vectors, such as retrovirus vectors or adenovirus vectors. Antisense oligonucleotides have a chain length of at least 10 bp or more and normally 100 bp or less; and preferably 20 bp or more and 50 bp or less. Antisense oligonucleotides can be prepared, for example, using the phosphorothioate method (Stein "Physicochemical properties of phosphorothioate oligodeoxynucleotides." Nucleic Acids Res. 16:3209-3221 (1988)) based on the nucleotide sequence information of SEQ ID NO: 1 or SEQ ID NO: 3.

The application of such antisense nucleotides to the gene therapy of disorders caused by proteins comprising the amino acid sequence of SEQ ID NO: 2 or SEQ ID NO: 4 can also be considered. When used for gene therapy, administration to patients by ex vivo methods, in vivo methods, and so on can be performed, for example, using viral vectors such as retrovirus vectors, adenovirus vectors, and adeno-associated virus vectors; and non-viral vectors such as liposomes.

Furthermore, the phosphatase-binding antibodies used in this invention can be used as agents for inhibiting the CREB dephosphorylation reaction, agents for suppressing enhancement of cell-damaging effect, and as preventive and therapeutic agents for disorders relating to phosphatases, such as memory disorders and/or neurodegenerative disorders. The antibodies of this invention that may be used as agents for inhibiting a CREB dephosphorylation reaction, agents for suppressing enhancement of the cell-damaging effect, or as preventive or therapeutic agents for memory disorders and/or neurodegenerative disorders, are antibodies against a protein of any one of the following (a) to (d):

(a) a protein comprising the amino acid sequence of SEQ ID NO: 2 or SEQ ID NO: 4;

(b) a protein that is functionally equivalent to the protein of (a) and which is encoded by a DNA that hybridizes under stringent conditions with a DNA comprising the nucleotide sequence of SEQ ID NO: 1 or SEQ ID NO: 3;

(c) a protein comprising the amino acid sequence of SEQ ID NO: 2 or SEQ ID NO: 4, wherein one or more amino acids of the sequence have been substituted, deleted, inserted, and/or added, and where the protein is functionally equivalent to the protein of (a); and (d) a protein comprising an amino acid sequence with 90% or higher homology to the amino acid sequence of SEQ ID NO: 2 or SEQ ID NO: 4, wherein the protein is functionally equivalent to the protein of (a).

The type of antibodies used in this invention is not particularly limited, and includes polyclonal antibodies, monoclonal antibodies, and fragments thereof which comprise antigen affinity. In addition, all classes of antibody are included. Furthermore, specialized antibodies, such as humanized antibodies, are also included.

Polyclonal antibodies can be obtained by immunizing animals with a protein of any one of the aforementioned (a) to (d), or with partial peptides thereof ("Current protocols in Molecular Biology", edit. Ausubel et al. (1987) Publish. John Wiley & Sons. Sections 11.12-11.13).

On the other hand, monoclonal antibodies can be obtained from hybridoma cells, which are obtained by immunizing animals using these proteins or partial peptides, and fusing the antibody-producing cells with myeloma cells and the like ("Current protocols in Molecular Biology", edit. Ausubel et al. (1987) Publish. John Wiley & Sons. Sections 11.4-11.11).

When using antibodies on a patient for preventive or therapeutic purposes, human antibodies or humanized antibodies are preferred for their low immunogenicity. Human antibodies can be prepared by immunizing mice whose immune system has been replaced with that of a human (e.g. "Functional transplant of megabase human immunoglobulin loci recapitulates human antibody response in mice", Mendez, M. J. et al. (1997) Nat. Genet. 15:146-156). Furthermore, humanized antibodies can be prepared by genetic recombination using the hypervariable region of a monoclonal antibody (Methods in Enzymology 203:99-121 (1991)).

A protein of any one of the aforementioned (a) to (d), and specifically, the phosphatase-binding antibody of this invention, may be used for purifying phosphatases, and also for testing and diagnosing expression abnormalities or structural abnormalities in these phosphatases. Specifically, the presence of expression and structural abnormalities can be examined and diagnosed, for example, by extracting proteins from tissues, blood, cells, and such, and then detecting the aforementioned proteins using methods such as Western blotting, immunoprecipitation, ELISA, and such.

Compounds isolated based on this invention become candidates for compounds that promote CREB's transcriptional activity in a living body. These compounds are useful as pharmaceutical agents for preventing and treating disorders relating to the aforementioned proteins. Specifically, compounds useful as pharmaceutical agents, therapeutic agents, and preventive agents for improving a wide variety of memory disorders and/or neurodegeneration in which CREB's transcriptional activity is involved can be evaluated using the evaluation methods of this invention.

Alternatively, compounds isolated based on this invention become candidates for compounds that regulate enhancement of cell damage in vivo. These compounds are useful as pharmaceutical agents for the prevention and treatment of disorders relating to the aforementioned proteins. Specifically, compounds useful as pharmaceutical agents, therapeutic agents, and preventive agents for improving a wide variety of cell damages in which cell-damaging enhancing activity is involved can be evaluated using the evaluation methods of this invention.

The evaluation methods of this invention can be used for methods of screening for compounds that comprise the activity of interest, and for characterizing compounds.

Compounds screened based on the above-mentioned evaluation method are useful as agents for inhibiting the CREB dephosphorylation reaction, or agents for suppressing enhancement of cell-damaging effect. Inhibitory agents for a CREB dephosphorylation reaction can be used for treating and preventing various disorders accompanying apoptosis caused by CREB activation. Furthermore, agents inhibiting enhancement of cell-damaging effect are useful for treating and preventing various disorders caused by enhancement of cell-damaging effect. Examples of such disorders include the following: myocardial infarction, myocarditis, viral hepatitis, alcoholic hepatitis, liver cirrhosis, insulin-dependent diabetes (due to the immunoreactive cell death of Langerhans cell pancreatic islets), and cerebral infarction.

Compounds screened based on the above-mentioned evaluation methods are considered to improve memory disorders and/or neurodegeneration, and to be useful as pharmaceutical agents for the prevention or treatment of a wide variety of neural disorders.

In the present invention, "memory disorders and/or neurodegenerative disorders" refers to disorders that are improved by regulation of CREB activity and by suppression of enhanced cell damage in neurons. For example, since increased CREB activity is linked to anti-apoptosis activity in neurons, the inhibitory agents for the dephosphorylation reaction, obtainable by the methods of screening of this invention, are useful for treating and preventing the following disorders: dementia due to cerebrovascular accident, multiple minimal brain infarction, cerebral thrombosis, cerebral infarction, cerebral hemorrhage, neurodegenerative disorders (Alzheimer's and such), Huntington's disease, and dentatorubropallidoluysian atrophy.

Since all of the above-mentioned disorders are accompanied by cell damage, compounds selected by this invention that suppress the enhancement of cell damage can be similarly used for the treatment and prevention of disorders such as those mentioned above.

In the present invention, when compounds are used as pharmaceutical agents, the compounds themselves may be used as pharmaceutical agents, or they may be formulated by known pharmaceutical methods. For example, they can be formulated by appropriate combination with pharmaceutically acceptable carriers or vehicles, and more specifically, with known substances used for formulation, such as sterilized water, physiological saline, vegetable oil, emulsifiers, and suspending agents.

Administration to patients can be performed by known methods, such as intraarterial injection, intravenous injection, and subcutaneous injection. The dose is variable depending on body weight, age, and the symptoms of the patient, as well as the method of administration and such, but one skilled in the art can appropriately select an adequate dose. Furthermore, if the compound is encoded by a polynucleotide such as DNA, the polynucleotide encoding the compound may be used for gene therapy by incorporation into a gene therapy vector.

In addition, the present invention relates to model animals with regulated CREB phosphorylation status. These model animals comprise a transgenic non-human animal with regulated expression of a protein that catalyzes the aforementioned CREB dephosphorylation reaction. The present inventors elucidated that the aforementioned proteins catalyze the CREB dephosphorylation reaction. Based on this finding, CREB's phosphorylation status can be regulated by regulating the expression of the aforementioned proteins.

CREB phosphorylation is decreased in the living body of an animal transferred with a gene encoding a protein catalyzing the aforementioned dephosphorylation reaction. As a result, it is expected that the transcriptional activity of CREB is decreased, and that memory disorders, neurodegeneration, and such will occur. Compounds that alleviate these conditions may thus be evaluated by using these animals as models.

Furthermore, the CREB phosphorylation level is enhanced in animals with impaired expression of proteins that catalyze the aforementioned CREB dephosphorylation reaction. As a result, a condition where CREB's transcriptional activity is enhanced can be created. Such animals are useful as models for discovering molecules and such which are necessary for maintaining memories and neurons. In the present invention, animals with impaired expression include animals in which expression of a protein is repressed (knockout), animals in which recombination to another gene has been carried out (knock-in), and animals in which the amino acid sequence of a protein has been altered to decrease its activity.

Alternatively, the present invention relates to model animals in which cell-damaging effect has been regulated. The model animals comprise transgenic non-human animals with regulated expression of the aforementioned proteins that enhance cell-damaging effect. The present inventors showed that the aforementioned proteins enhance cell-damaging effect. Based on this finding, cell-damaging effect can be regulated by regulating the expression of the aforementioned proteins.

Cell-damaging effect in a living body is enhanced in animals to which genes encoding the aforementioned protein that enhances the cell-damaging effect have been transfected. As a result, memory disorders, neurodegeneration, and such are expected to occur, since cells are placed under conditions prone to cell damage. Using such animals as models, compounds that alleviate those cell damages may be evaluated.

Furthermore, enhancement of cell damage is suppressed in animals whose expression of the aforementioned protein that enhances cell damage has been weakened. Such animals are useful as models for discovering molecules and such required for maintaining memory and neurons.

Methods for obtaining transgenic animals in which expression of the desired gene has been regulated are well known (for example, see U.S. Pat. No. 4,736,866; Nikkei Science, Vol. 25, No. 6: 40-50 (1995)): specifically, introduction of an exogenous gene, or deletion of a target gene using techniques such as homologous recombination, in the early stages of cell differentiation. An individual that develops from this embryo becomes a chimeric animal comprising genetically manipulated cells. When an offspring of the chimeric animal carries a genetic mutation, that individual is a transgenic animal comprising a heterozygous genetic mutation. By crossing heterozygous transgenic animals with each other, a transgenic animal comprising a homozygous mutation can be obtained.

All references of prior art cited herein are incorporated into this description by reference.

BEST MODE FOR CARRYING OUT THE INVENTION

Figure 1:
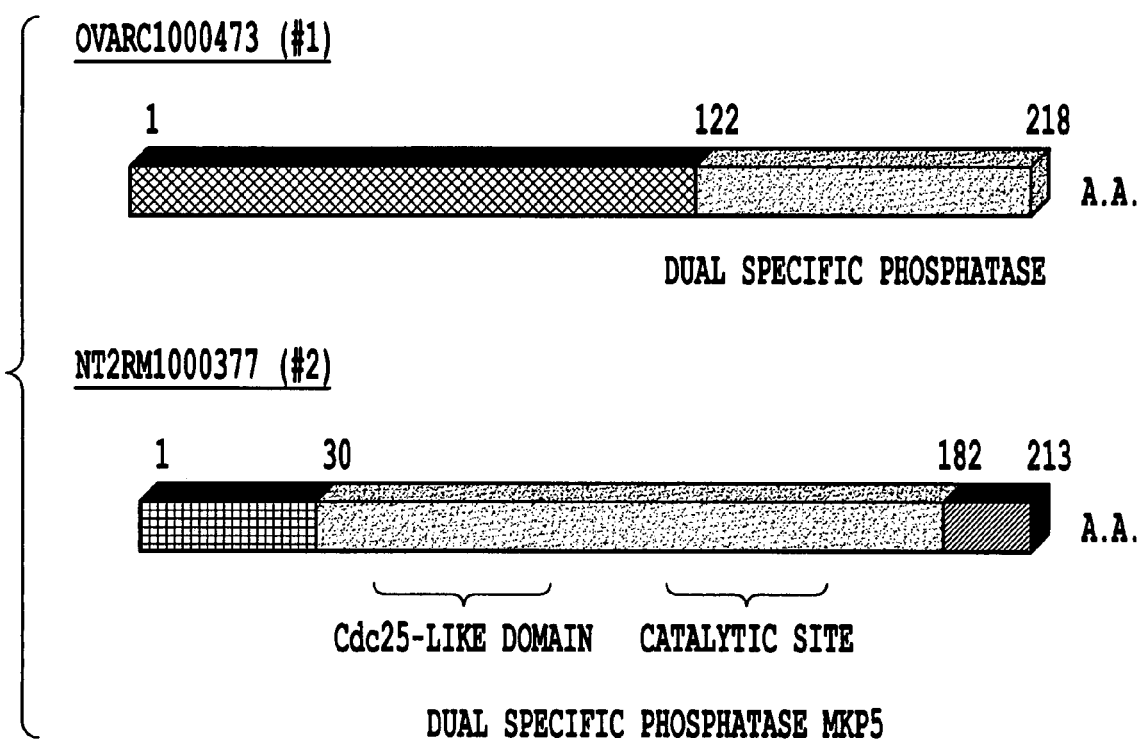
FIG. 1 shows the structures of the proteins encoded by OVARC1000473 (SEQ ID NO: 1/above) and NT2RM1000377 (SEQ ID NO: 3/below), which are clones that suppress the increase of transcriptional activity of CREB. OVARC1000473 (GenBank BC004176) is isolated from the ovary. Of the total of 218 amino acid residues encoded by this gene, the C-terminal amino acids (122-218) have 34% homology to a dual specific phosphatase (Swissplot Q16690), and a phosphatase catalytic site has been recognized in the sequence from amino acid numbers 159 to 176 of the dual specific phosphtase (Keyse S. M., Biochem. Biophys. Acta (1995, March 16) 1265 (2-3):152-60) (FIG. 1, upper panel). NT2RM1000377 (GeneBank AK022513) is a gene isolated from human neuroblast NT2 cells. The amino acid sequence encoded from this gene includes a cdc25-like domain (indicated) and a catalytic site (indicated) (FIG. 1, bottom panel).

Herein below, the present invention is specifically described using examples, however, it is not to be construed as being limited thereto.

EXAMPLE 1

Effect of Phosphatase-related Genes on the Increase of Transcriptional Activity due to Forskolin (1) Helix Clone-derived Expression Vectors and Reporter Expression Vectors From a Helix Research Institute cDNA library, or the like, six phosphatase-related genes comprising a phosphatase motif were selected using the BLAST algorithm. Each of the obtained genes was cloned with fixed cDNA directionality into vector pME18SFL3 (GenBank AB009864, Expression Vector), which had been cleaved with DraIII, to yield a phosphatase-related gene expression vector.

pME18DFL3-377 is an expression vector in which a gene derived from the Helix clone NT2RM1000377 has been ligated downstream of the CMV IE promoter of pME18SFL3. pME18DFL3-473 is an expression vector in which a gene derived from the Helix clone OVARC1000473 has been ligated downstream of the CMV IE promoter.

pCRE-Luc (Stratagene) is a reporter expression vector in which firefly luciferase reporter gene has been ligated downstream of a promoter comprising a CRE element. pRL3-SV40 (Promega) is a reporter expression vector in which Renilla luciferase gene has been ligated downstream of an SV40 early promoter.

(2) Gene Transfer into PC12 Cells

10 µg of pCRE-Luc (Stratagene), 0.2 µg of pRL3-SV40, and 10 µg of phosphatase-related gene expression vector were added to 0.5 mL of opti-MEM media (invitrogen), and this was left to stand at. room temperature for five minutes. Herein, pME18DFL3-377 and pME18DFL3-473 were used as Helix clone-related gene expression vectors. Alternatively, pBluescript was used as a control. Meanwhile, 0.5 mL of opti-MEM media (invitrogen) and 20 µL of lipofectamine 2000 (invitrogen) were mixed and left to stand at room temperature for three minutes. These vector mixture solutions and the lipofectamine 2000 diluent were mixed, and then incubated at room temperature for 20 minutes to produce a conjugate of Lipofectamine 2000 and the vector. $1.0 \times 10^6$ PC12 cells were plated into a culture flask (25 cm², Corning) pre-coated with collagen type I, and then incubated overnight at 37° C. in 3 mL of RPMI1640 media containing 10% FCS. The above conjugate was added dropwise to these PC12 cells, and this was further cultured overnight at 37° C.

(3) Measurement of CREB's Transcriptional Activity

Transgenic cells, obtained by the method of (2) mentioned above, were plated at $5 \times 10^5$ cells per well on a 96-well plate coated with collagen type I (Nippon Meat Packers, Inc.), and then cultured overnight at 37° C. Thereafter, the cells were washed with RPMI1640 media, forskolin (Sigma) was added at a concentration of 10 µM, and this was cultured for another eight hours at 37° C. CREB activity was then measured by the following method. Specifically, the supernatant was removed by suction, and the cells were dissolved using 20 µL of lysis buffer (12.5 mM Tris-HCl (pH 7.4), 1% Triton X). To this, 50 µL of firefly luciferase substrate solution and 50 µL of Renilla luciferase substrate solution (in the Dual luciferase assay kit (Promega)) were added, and chemiluminescence was measured. Wallac 1420 ARVOsx (AmershamPharmacia) was used as a measurement instrument. The ratio of Renilla luciferase activity to firefly luciferase activity was taken as the CREB's transcriptional activity.

Figure 2:
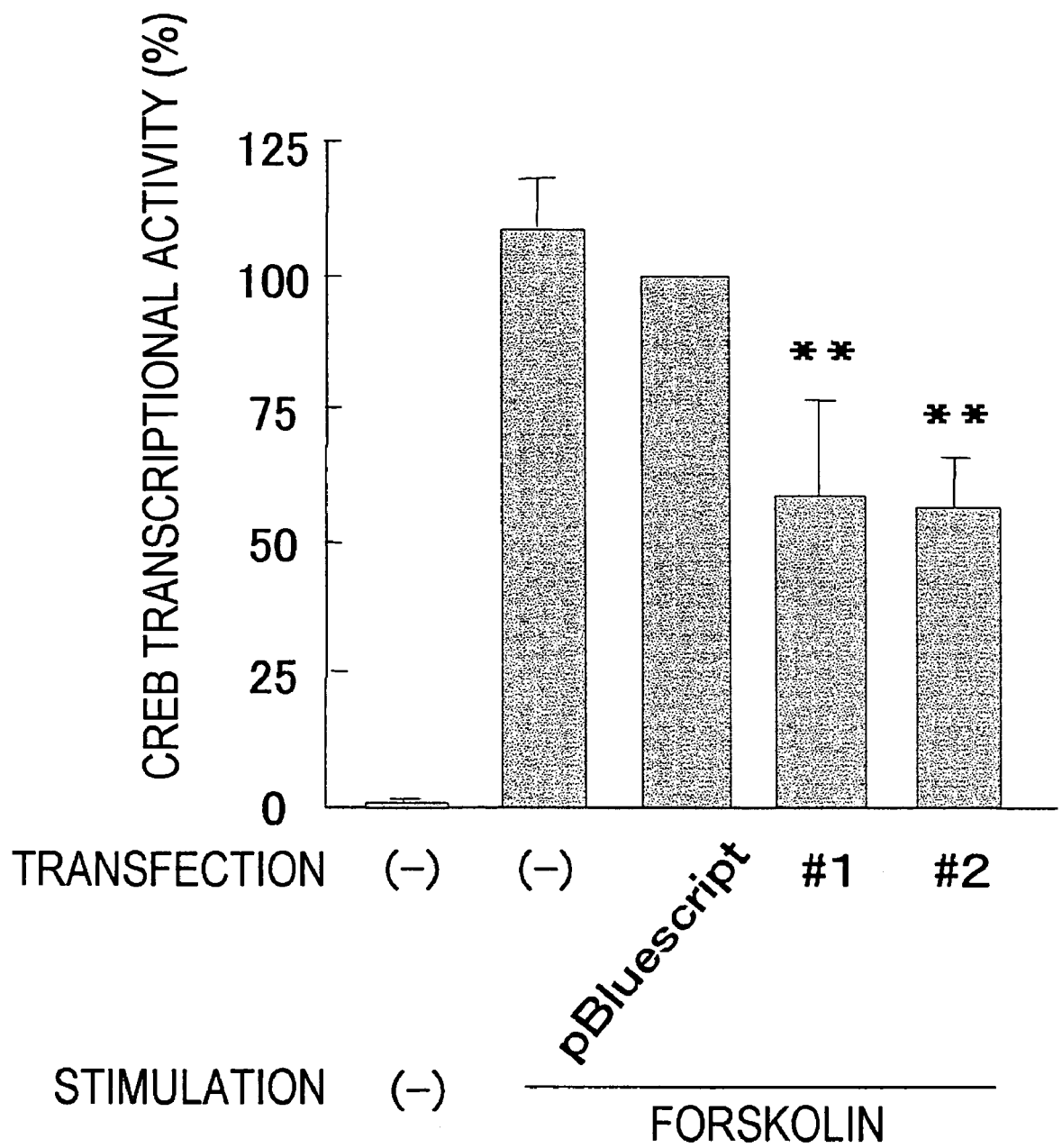
FIG. 2 shows the effect of OVARC1000473 (#1) and NT2RM1000377 (#2) on forskolin-induced increase in CREB's transcriptional activity. The vertical axis indicates relative CREB's transcriptional activity (%). Transfer of pRL3-SV40 alone, without forskolin stimulation, is set to 0%. Transformation performed with pCRE-Luc, pRL3-SV40, and pBluescript in the presence of forskolin stimulation is set as 100%.

FIG. 2 shows the results of measuring CREB's transcriptional activity in this manner, and is an average of triplicate experiments. The vertical axis shows relative CREB's transcriptional activity (%), where an absence of pCRE-Luc transfection is taken as 0%, and transformation with pCRE-Luc and pBluescript and subsequent stimulation with forskolin is taken as 100%. Increase of CREB's transcriptional activity by forskolin stimulation was found to be significantly suppressed in PC12 cells transfected with genes derived from Helix clones OVARC1000473 and NT2RM1000377 respectively. From this result, and from the structural characteristics of the amino acid sequence of the expected protein, these two genes were identified as genes encoding proteins comprising the phosphatase activity of catalyzing CREB dephosphorylation.

EXAMPLE 2

Construction of a Drug Screening System

10 μg of pCRE-Luc (Stratagene), 2 μg of pRL3-SV40, and 0 μg to 10 μg of pME18DFL3-377 were transfected into PC12 cells using a method similar to that of Example 1 (2). As a control vector, 0 μg to 10 μg of pME18SFL3 was used, and the total amount was adjusted with pME18DFL3-377 to 10 μg. These transfected cells were plated at $5 \times 10^5$ cells per well on a 96-well plate coated with collagen type I (Nippon Meat Packers, Inc.), and then cultured overnight at 37° C. Thereafter, the cells were washed with RPMI1640 media, mouse 2.5S NGF (Promega) was added at a concentration of 10 ng/mL, and this was cultured for another eight hours at 37° C. CREB activity was then measured using the following method: Specifically, the supernatant was removed by suction, and the cells were dissolved using 20 μL of lysis buffer (12.5mMTris-HCl (pH7.4), 1%Triton-X). 50 μL of firefly luciferase substrate solution and 50 μL of Renilla luciferase substrate solution (in the Dual luciferase assay kit (Promega)) were added to this material, and chemiluminescence was measured. Wallac 1420 ARVOsx (AmershamPharmacia) was used as a measurement instrument. The ratio of Renilla luciferase activity to firefly luciferase activity was taken as the CREB's transcriptional activity.

Figure 3:
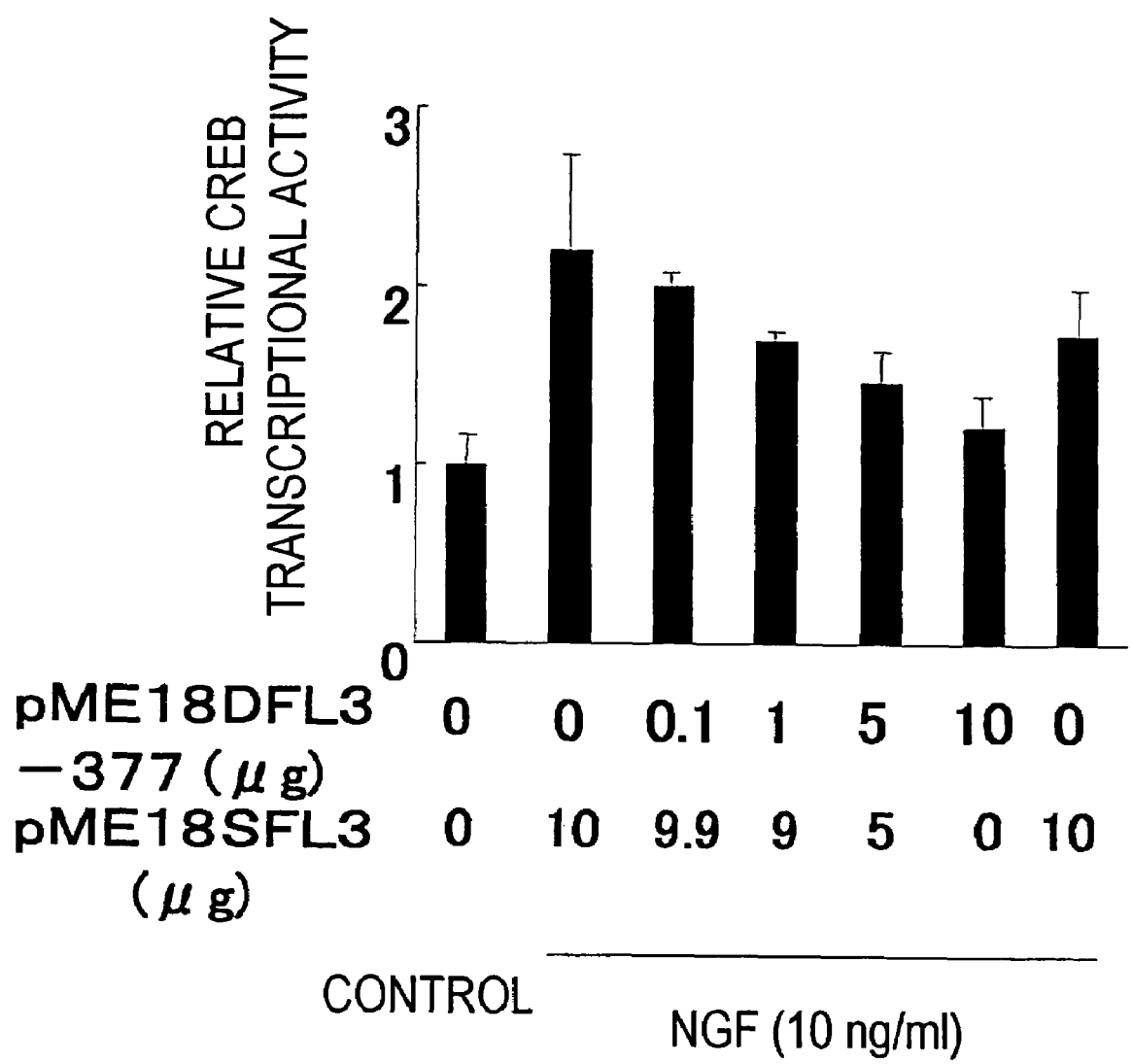
FIG. 3 shows that increase of CREB's transcriptional activity due to NGF stimulation is significantly suppressed depending on the amount of pME18DFL3-377 expression vector of NT2RM1000377, transferred to PC12 cells. The vertical axis indicates relative CREB's transcriptional activity. The relative activity in the case of transfection with pRL3-SV40 alone, without NGF stimulation, is set to 0. The relative activity in the case of transfection with only pCRE-Luc and pRL3-SV40, without NGF stimulation, is set to 1.

FIG. 3 shows the results of CREB's transcriptional activity measured in this manner, and is an average of triplicate experiments. The vertical axis indicates relative CREB's transcriptional activity. The relative activity of cells transfected with only pRL3-SV40 alone in the absence of NGF stimulation is represented as 0. The relative activity of cells not transfected with pME18DFL3-377 and pME18SFL3, but transfected with only pCRE-Luc and pRL3-SV40 in the absence of NGF stimulation is represented as 1. In PC12 cells to which a Helix clone NT2RM1000377-derived gene has been transfected, the increase of CREB's transcriptional activity due to NGF addition was found to be significantly suppressed, depending on the amount of pME18DFL3-377 expression vector used for gene transfection. This fact suggests that NT2RM1000377-derived gene products operate in a suppressive manner against CREB's transcriptional activity. Furthermore, in the above-mentioned assay system, by adding a novel compound along with NGF, and measuring the effect of that addition as CREB's transcriptional activity, a system for screening for new pharmaceutical agents that ameliorate suppression of CREB's transcriptional activity can be constructed.

EXAMPLE 3

Potentiation Effect Towards Cell Damage

10 μg of pCRE-Luc (Stratagene), 2 μg of pRL3-SV40, and 10 μg of pME18DFL3-377 were transfected into PC12 cells using a method similar to that of Example 1 (2). As a control, 10 μg of pBluescript was used instead of pME18DFL3-377.

These transgenic cells were plated at $5 \times 10^5$ cells per well on a 96-well plate coated with collagen (Nippon Meat Packers, Inc.), and this was then cultured overnight at 37° C. Thereafter, this was washed with RPMI1640 media, mouse 2.5S NGF (Promega) was added at a concentration of 0 ng/mL, 1 ng/mL, or 10 ng/mL, and this was cultured for another eight hours at 37° C.

The cells were washed once with the media, and then incubated for 18 hours by adding 10 nM of thapsigargin (Sigma) and nerve growth factor (NGF) to DMEM media (Sigma) containing 5% Horse serum and 5% FCS.

PC12 cells are of the strain derived from rat adrenal pheochromocytoma. Thapsigargin is an inhibitor of sarcoplasmic reticulum calcium pumps (sarcoplasmic reticulum and endoplasmic reticulum $Ca^{2+}$ ATPase pumps). Administration of thapsigargin induces apoptosis of PC12 cells. Furthermore, NGF differentiates PC12 cells into neuron-like cells. This differentiation process stimulates transcriptional activity of CREB. Therefore, by culturing pME18DFL3-377-transformed PC12 cells in the presence of thapsigargin and NGF, NT2RM1000377s's apoptosis-inducing effect, and CREB's effect on transcriptional activity, can be observed.

Cell damage was measured using a Cytotoxicity Detection Kit (LDH) (Roche) to measure the activity of lactate dehydrogenase (LDH) released outside of a cell due to cell membrane damage. 75 μL from the Cytotoxicity Detection Kit was added to 75 μL of cell culture supernatant after incubation, and this was reacted at room temperature for 20 minutes. Absorbance at 490 nm was then measured.

Figure 4:
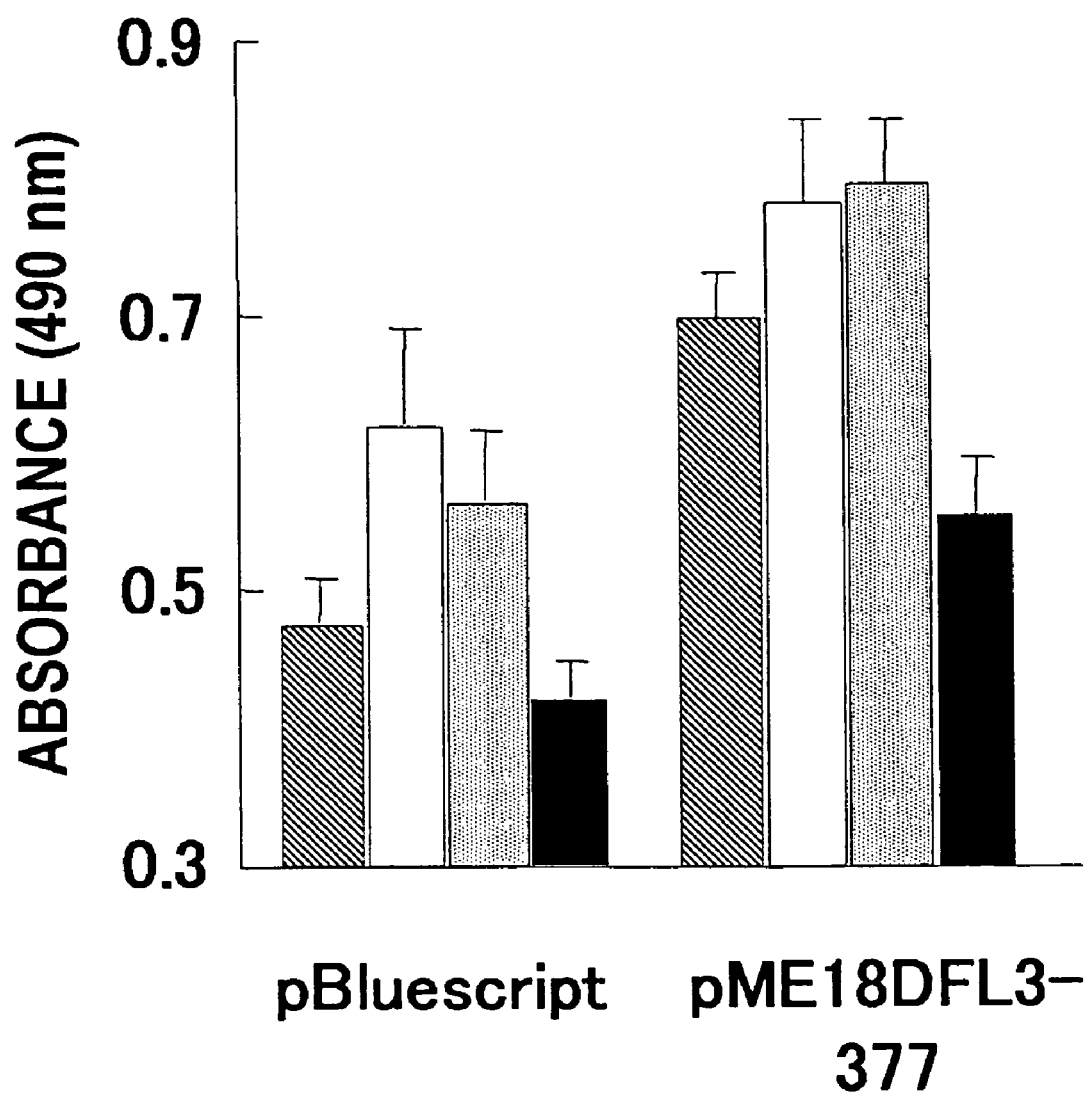
FIG. 4 shows the enhancement of cell damage by thapsigargin in PC12 cells to which a NT2RM1000377-derived gene expression vector, pME18DFL3-377, has been transfected.

FIG. 4 shows the results of CREB's transcriptional activity measured in this manner. In PC12 cells to which the Helix clone NT2RM1000377-derived gene has been transfected, cell damage effect by thapsigargin was shown to be enhanced.

INDUSTRIAL APPLICABILITY

The present invention identified OVARC1000473 (SEQ ID NO: 1) and NT2RM1000377 (SEQ ID NO: 3) as clones that show suppression against the activation of CREB by forskolin. Furthermore, this invention provides evaluation methods that use these genes, and/or proteins encoded by these genes. The evaluation methods of the present invention enable the evaluation of compounds that inhibit the effect of suppressing CREB phosphorylation. Compounds selected by the evaluation methods of the present invention comprise the effect of increasing CREB's transcriptional activity. Such compounds, for example, improve memory disorders and neurodegeneration, and are useful as pharmaceutical agents against a wide variety of neural disorders. The protein encoded by the above-mentioned gene, NT2RM1000377, was confirmed to comprise the effect of enhancing cell damage. This protein is clearly an important target molecule for prevention and therapy of disorders accompanying cell damage.

Furthermore, the present invention elucidated that cell-damaging effect can be regulated by regulating the activity of the above-mentioned proteins. For example, the progression of neuron hypofunction can be prevented by suppressing the expression and activity of the protein encoded by NT2RM1000377. Therefore, compounds comprising the effect of inhibiting the expression and activity of NT2RM1000377 improve memory disorders and neurodegeneration, and are useful as pharmaceutical agents for a wide variety of neural disorders.

Alternatively, cell-damaging effect can be enhanced by stimulating the expression and activity of NT2RM1000377. More specifically, the cell-damaging effect of thapsigargin can be enhanced by the action of the protein encoded by NT2RM1000377. The compound thapsigargin is being tested for application in tumor therapy. Therefore, proteins comprising the effect of strengthening this action are useful in tumor therapy. More specifically, proteins comprising such an effect can be used in the treatment of neurocytomas and such.

The invention claimed is:

1. A method for detecting a compound which inhibits dephosphorylation of a cAMP responsive element binding protein (CREB), wherein the method comprises
   contacting a protein with (A) CREB and a protein kinase that phosphorylates CREB to phosphorylate CREB, or (B) a phosphorylated CREB in the presence or absence of a test compound, measuring the phosphorylation level of CREB;
wherein a higher level of phosphorylation in the presence of the test compound compared to the absence of the compound is indicative that the compound inhibits dephosphorylation of CREB, and:
   wherein (1) the protein comprises the amino acid sequence of SEQ ID NO: 4, (2) the protein is encoded by a polynucleotide that hybridizes under stringent conditions with the full length complement of SEQ ID NO: 3, wherein the stringent conditions comprise a washing step in 0.1×SCC and 0.1% SDS at 65° C., and wherein the protein has CREB dephosphorylation activity; or (3) the protein comprises an amino acid sequence with at least 95% homology to the amino acid sequence of SEQ ID NO: 4, wherein the protein has CREB dephosphorylation activity.

2. The method of claim 1, wherein the CREB phosphorylation level is measured, using as an index, the transcriptional activity of a CREB-regulated gene.

3. The method of claim 1, wherein the protein comprises the amino acid sequence of SEQ ID NO:4.

4. The method of claim 1, wherein, the protein is encoded by a polynucleotide that hybridizes under stringent conditions with the full length complement of SEQ ID NO: 3, wherein the stringent conditions comprise a washing step in 0.1×SCC and 0.1% SDS at 65° C. and wherein the protein has CREB dephosphorylation activity.

5. The method of claim 1, wherein the protein comprises an amino acid sequence with at least 95% homology to the amino acid sequence of SEQ ID NO: 4, wherein the protein has CREB dephosphorylation activity.

6. The method of claim 1, wherein the method comprises contacting the protein in the presence of CREB and a kinase to phosphorylate CREB in the presence or absence of the test compond.

7. The method of claim 6, wherein the CREB phosphorylated site is a serine at position 133 of CREB.

8. The method of claim 1, wherein the method comprises contacting a test compound with a protein in the presence of a phosphorylated CREB.

9. The method of claim 1, wherein the CREB phosphorylated site is a serine at position 133 of CREB.

10. The method of claim 1, wherein the contacting occurs in a cell.

11. The method of claim 10, wherein the cell comprises a polynucleotide encoding CREB.

12. The method of claim 10, wherein the cell comprises a polynucleotide encoding the protein.

13. The method of claim 11, wherein the cell comprises a polynucleotide encoding the protein.

* * * * *